(12) United States Patent
Kroll et al.

(10) Patent No.: US 7,414,534 B1
(45) Date of Patent: Aug. 19, 2008

(54) METHOD AND APPARATUS FOR MONITORING INGESTION OF MEDICATIONS USING AN IMPLANTABLE MEDICAL DEVICE

(75) Inventors: Mark W. Kroll, Simi Valley, CA (US); Alan B. Vogel, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 137 days.

(21) Appl. No.: 10/985,298

(22) Filed: Nov. 9, 2004

(51) Int. Cl.
G08B 23/00 (2006.01)
(52) U.S. Cl. ............. 340/573.1; 128/903; 600/302
(58) Field of Classification Search .......... 340/573.1, 340/572.1, 573.3, 10.1, 10.3; 128/899, 903; 600/302; 607/60
See application file for complete search history.

(56) References Cited

U.S. PATENT DOCUMENTS

| | | | |
|---|---|---|---|
| 5,328,460 A | 7/1994 | Lord et al. ............. 604/67 |
| 5,476,483 A | 12/1995 | Bornzin et al. ............. 607/17 |
| 5,836,987 A | 11/1998 | Baumann et al. ............. 607/17 |
| 5,935,081 A | 8/1999 | Kadhiresan ............. 600/513 |
| 5,963,132 A | 10/1999 | Yoakum ............. 340/572.1 |
| 5,963,136 A | 10/1999 | O'Brien ............. 340/573.1 |
| 5,973,600 A | 10/1999 | Mosher, Jr. ............. 340/572.8 |
| 6,115,636 A * | 9/2000 | Ryan ............. 128/903 |
| 6,128,534 A | 10/2000 | Park et al. ............. 607/17 |
| 6,150,942 A | 11/2000 | O'Brien ............. 340/573.1 |
| 6,249,705 B1 | 6/2001 | Snell ............. 607/59 |
| 6,329,920 B1 * | 12/2001 | Morrison et al. ............. 340/573.3 |
| 6,366,206 B1 * | 4/2002 | Ishikawa et al. ............. 340/573.1 |
| 6,401,071 B1 * | 6/2002 | Hogan ............. 705/2 |
| 6,477,406 B1 | 11/2002 | Turcott ............. 600/518 |
| 6,512,952 B2 | 1/2003 | Stahmann et al. ............. 607/9 |
| 6,519,493 B1 | 2/2003 | Florio et al. ............. 607/9 |
| 6,527,729 B1 | 3/2003 | Turcott ............. 600/528 |
| 6,529,127 B2 * | 3/2003 | Townsend et al. ............. 340/505 |
| 6,611,556 B1 * | 8/2003 | Koerner et al. ............. 375/224 |
| 6,628,988 B2 | 9/2003 | Kramer et al. ............. 607/9 |
| 6,643,546 B2 | 11/2003 | Mathis et al. ............. 607/9 |
| 6,658,294 B1 | 12/2003 | Zadeh et al. ............. 607/28 |
| 6,811,533 B2 * | 11/2004 | Lebel et al. ............. 600/300 |
| 6,861,954 B2 * | 3/2005 | Levin ............. 340/572.1 |
| 7,022,070 B2 * | 4/2006 | Ebner et al. ............. 600/301 |

(Continued)

FOREIGN PATENT DOCUMENTS

WO          WO 02/05039 A1          1/2002

(Continued)

*Primary Examiner*—John A Tweel, Jr.

(57) ABSTRACT

An implantable medical device, such as a pacemaker or implantable cardioverter defibrillator (ICD), is configured to automatically detect ingestion of medications to verify that prescribed medications are taken in a timely manner and at the correct dosage. Briefly, individual pills are provided with miniature radio frequency identification (RFID) devices capable of transmitting RFID tag signals, which identify the medication contained within the pill and its dosage. The implanted device is equipped with an RFID transceiver for receiving tag signals from a pill as it is being ingested. The implanted system decodes the tag to identify the medication and its dosage, then accesses an onboard database to verify that the medication being ingested was in fact prescribed to the patient and to verify that the correct dosage was taken. Warning signals are generated if the wrong medication or the wrong dosage was taken. Therapy may also be automatically adjusted. Non-RF-based ID devices are also described, which instead transmit ID data via biphasic current pulses.

15 Claims, 14 Drawing Sheets

U.S. PATENT DOCUMENTS

| | | | |
|---|---|---|---|
| 7,071,827 B2 * | 7/2006 | Carroll | 340/573.1 |
| 2002/0017996 A1 | 2/2002 | Niemiec | 340/573.1 |
| 2002/0038392 A1 | 3/2002 | De La Huerga | 710/8 |
| 2003/0058110 A1 | 3/2003 | Rich | 340/573.1 |
| 2003/0130703 A1 | 7/2003 | Florio et al. | 607/11 |
| 2003/0130704 A1 | 7/2003 | Florio et al. | 607/11 |
| 2004/0236193 A1 * | 11/2004 | Sharf | 600/302 |
| 2005/0131281 A1 * | 6/2005 | Ayer et al. | 600/302 |

FOREIGN PATENT DOCUMENTS

WO    WO 2006/116718 A2    11/2006

\* cited by examiner

| PRESCRIPTION DRUG/RFID TAG DATABASE | |
|---|---|
| DRUG/DOSAGE | RFID TAG |
| PROCAINAMIDE/250 MG CAPSULE | RFID DRUG TAG #1 |
| PROCAINAMIDE/375 MG CAPSULE | RFID DRUG TAG #2 |
| PROCAINAMIDE/500 MG CAPSULE | RFID DRUG TAG #3 |
| DILTIAZEM/30 MG TABLET | RFID DRUG TAG #4 |
| DILTIAZEM/60 MG TABLET | RFID DRUG TAG #5 |
| . . . | |

| CURRENT PATIENT PRESCRIPTION DATABASE | |
|---|---|
| PRESCRIBED DRUG/DOSAGE | FREQUENCY |
| PROCAINAMIDE/375 MG CAPSULE | ONCE PER DAY |
| DILTIAZEM/30 MG TABLET | TWICE PER DAY |
| . . . | |

| MEDICATION INTAKE RECORD DATABASE | | |
|---|---|---|
| DRUG TAKEN | DOSAGE TAKEN | DATE/TIME |
| PROCAINAMIDE | 375 MG | 11:23 AM AUG. 23 2004 |
| DILTIAZEM | 30 MG | 1:15 PM AUG. 25 2004 |
| . . . | | |

FIG. 3

METHOD AND APPARATUS FOR MONITORING INGESTION OF MEDICATIONS USING AN IMPLANTABLE MEDICAL DEVICE

FIELD OF THE INVENTION

The invention generally relates to implantable medical devices and to techniques for verifying ingestion of prescribed medications using such devices.

BACKGROUND OF THE INVENTION

Every year, countless medications are prescribed to millions of patients to address a wide variety of medical conditions. It is often difficult, however, for physicians to ensure that appropriate dosages of prescribed medications are actually taken by their patients at the appropriate times. Many patients simply fail to take prescribed drugs—sometimes intentionally (perhaps because they want to avoid perceived side effects of the drugs)—sometimes unintentionally (perhaps because they simply forget to take the drugs or run out of the drugs). In other cases, the prescribed drug is taken, but with an incorrect dosage level. This may occur because the patient believes, contrary to the advice of the physician, that a stronger dosage would be beneficial or, more typically, because the patient has simply forgotten that he or she had already taken the medication and then takes an additional, unnecessary dose. These problems are particularly significant among the elderly, who may have a large number of ongoing prescriptions at any one time and who often show signs of short term memory loss. For many medical conditions, including serious heart conditions such as congestive heart failure (CHF), failure to take the prescribed dosage of the drug in a timely manner can have severe adverse consequences. Accordingly, it would be highly desirable to provide techniques, particularly for the benefit of the elderly, for automatically monitoring prescription drug intake to remind the patient if he or she has failed to take a prescribed drug in a timely manner or to warn the patient if the incorrect drug or incorrect dosage has been taken. It is to this end that the invention is generally directed.

Many elderly patients have implanted medical devices, such as pacemakers or implantable cardioverter defibrillators (ICDs), or are candidates for such devices. Increasingly, such devices are provided with the capability of generating warning signals to alert the patient to adverse medical conditions, such as the onset of particular heart problems, so that medical attention may be sought. See, for example, U.S. patent application Ser. No. 10/603,429, filed Jun. 24, 2003 of Wang, et al., entitled "System and Method for Detecting Cardiac Ischemia Using an Implantable Medical Device". Depending upon the implanted system, the warning signals may be transmitted to an external bedside monitor for alerting the patient or may be applied internally in the form of a perceptible warning signal generated, for example, by an implanted vibration device. In any case, it would be desirable to equip implantable medical devices with components for automatically monitoring prescription drug intake so that such warning devices can also be used to alert the patient if he or she fails to take a prescribed drug in a timely manner or takes the incorrect dosage of the drug. It is to these specific ends that particular aspects of the invention are directed.

SUMMARY

In accordance with one embodiment, a technique is provided for use in detecting the ingestion of drugs by a patient in which an implantable medical system is implanted. The implanted system senses a signal transmitted by an individual pill as it is being ingested and thereby detects ingestion of the pill based on the sensed signal.

In one example, individual pills are provided with miniature radio frequency identification (RFID) devices capable of transmitting RFID tag signals, which identify the medication contained within each respective pill, as well as its dosage. The implanted system is equipped with an RFID transceiver (or receiver in the case of active RFID medications) for sensing RFID tag signals emitted by the RFID device in the pill as it is being ingested. The implanted system decodes the RFID tag to identify the medication of the pill and its dosage. The device then accesses an onboard database listing patient prescriptions to verify that the medication being ingested was in fact prescribed to the patient and to verify that the correct dosage was taken. Warning signals are generated via an internal warning device or via a bedside monitor to alert the patient in case the wrong medication or the wrong dosage was taken. The device also periodically accesses the on-board database to identify any medications that were prescribed to the patient but were not taken in a timely manner and, if so, reminder signals ale generated, again using either an implanted warning device, bedside monitor, or both. If a bedside monitor is provided, the bedside monitor preferably forwards the various warning or reminder signals to the prescribing physician so he or she may be alerted as well. This is particularly desirable if it has been found that the patient has taken the wrong medication.

Preferably, the RFID device of each pill is coated with a suitable hermetic substance, such as ceramic, so as to be biocompatible and non-digestible. After the pill has been digested, the RFID device of the pill is merely passed from the body as waste and thereby discarded. For capsules, the circuitry of the RFID device may be formed on a flexible substrate that is wrapped around the perimeter of the capsule. For disk-shaped tablets, the circuitry of the RFID device may be attached to a flat base of the tablet. In any case, the RFID device preferably transmits the RFID tag via low frequency RF signals, which are capable of passing through the tissues of the patient from the esophageal track to the RFID transceiver of the implanted system.

The RFID devices in the pills may be passive or active. A passive RFID device has no on-board battery and transmits its RFID tag only in response to the temporary delivery of power from an RFID transceiver. An active RFID device has an on-board battery and transmits its RFID tag periodically, in which case the implanted device may simply include an RFID receiver as opposed to an RFID transceiver. For use with pills equipped with passive RFID devices, the RFID transceiver of the implanted system uses an antenna to transmit power to the pill via low frequency RF signals. The RFID device of the pill then uses the received power to transmit the RFID tag back to the transceiver. To reduce power consumption, the implanted system is preferably equipped with components capable of detecting when the patient is in the act of swallowing and only transmits RFID power signals via the antenna at such times. Swallowing may be identified, for example, based on certain patient movements detected by an accelerometer in combination with internal patient sounds detected by an acoustic sensor and further in combination with patient posture as detected by a posture detector. A patient sleep detector may also be used to detect sleep so as to deactivate the RFID transceiver while the patient is sleeping and hence not capable of orally ingesting medications. When used with pills equipped with active RFID devices, the implanted system may instead continuously monitor for possible RFID signals from pills being ingested; though, preferably, such monitoring is again only performed while the patient is found to be swallowing, so as to reduce processing demands within the implanted system.

In embodiments wherein the implantable system is a pacemaker or ICD, the drugs to be ingested are often heart medications, such as anti-arrhythmics, anti-thrombolytics, or the like. In such embodiments, if the implanted system determines that the patient has failed to take a prescribed heart medication in a timely manner, the system may automatically adjust pacing therapy in an attempt to compensate. For example, if the patient fails to take a drug prescribed for reducing the risk of atrial fibrillation (AF), the device may activate overdrive pacing in an attempt to reduce the likelihood that AF will occur. As another example, if the patient fails to take a drug prescribed for reducing the risk of ventricular fibrillation (VF), the device may pre-charge a shocking capacitor so that, should a life-threatening VF occur, a defibrillation shock can be delivered promptly, thus improving the patient's chance of survival. If the system is provided with an implanted drug pump, the pump may be controlled to deliver a quantity of stored medication in an attempt to compensate for medication that should have been taken orally. In this regard, the drug pump may be provided with a small "reserve" quantity of a critical medication. Hence, should the patient run out of critical medication that is to be taken orally, the implanted system can ensure that the patient receives at least some of the needed medication internally while the patient seeks to obtain more of the oral medication.

Although well suited for use with pacemakers or ICDs, the invention may be implemented using any of a wide range of other implantable medical devices, such as devices for stimulating or sensing portions of the brain, spinal cord, muscles, bones, nerves, glands or other body organs or tissues. The invention may alternatively be implemented as a dedicated device implanted solely for monitoring the ingestion of medications. Moreover, whereas miniaturized RFID devices are particularly well suited for transmitting suitable ID signals to the implanted system, other miniaturized transmission devices may instead be employed, such as non-RF based electronic ID (EID) devices. For example, a pill may be equipped to transmit an ID tag via a sequence of biphasic current pulses, which are conducted through the tissues of the body. The leads of the pacemaker or ICD are used to sense the biphasic current pulses so that the ID tag may then be decoded.

Also, whereas the invention is described herein primarily with respect to detecting the ingestion of prescription medications in the form of pills or tablets, principles of the invention may be applied for detecting intake of medications consumed via other means or for detecting the consumption of other items entirely, such as dietary supplements or the like.

BRIEF DESCRIPTION OF THE DRAWINGS

Further features and advantages of the invention may be more readily understood by reference to the following description taken in conjunction with the accompanying drawings, in which:

FIG. 3 is a block diagram illustrating database components for use with the technique of FIG. 2 for monitoring prescription drug intake;

DETAILED DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the descriptions that follow, like numerals or reference designators are used to refer to like parts or elements throughout.

Overview of Implantable RFID-based Medication Intake Monitoring System

Figure 1:
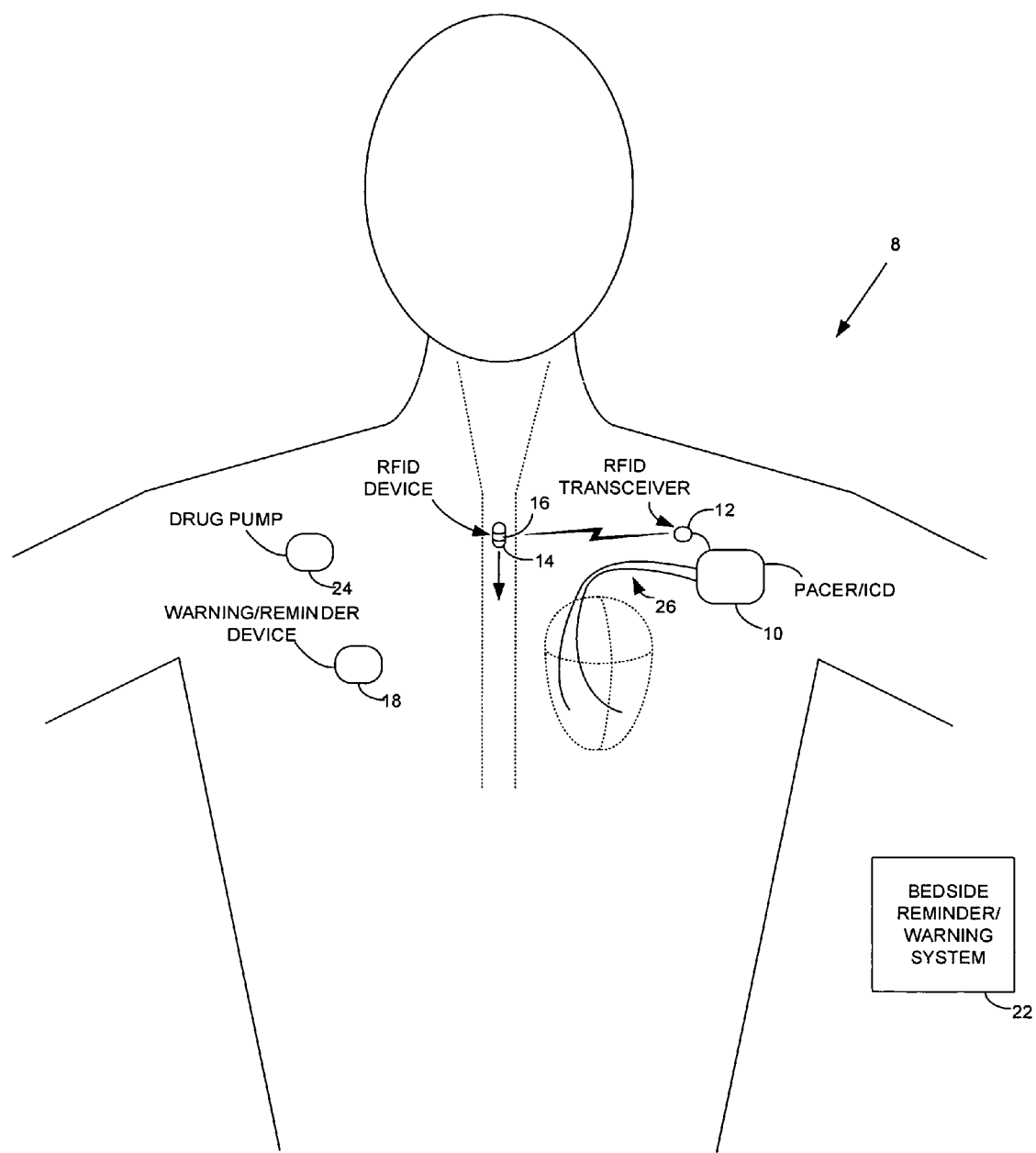
FIG. 1 illustrates pertinent components of an implantable RFID-based medication monitoring system having a pacemaker or ICD capable of detecting RFID tag signals transmitted by pills being ingested so as to monitor prescription drug intake.

FIG. 1 illustrates an implantable medical system 8 capable of: detecting ingestion of RFID-tagged medications; verifying the correct drug/dosage of the ingested medications; delivering any necessary warning or reminder signals if the correct drug/dosage of a prescribed medication has not been ingested in a timely manner; and controlling therapy in response thereto. Briefly, implanted system 8 includes a pacer/ICD 10 or other implantable medical device that utilizes an RFID transceiver (or simply a receiver) 12 to detect RFID tag signals from medications being ingested, such as exemplary capsule 14, which is equipped with a miniaturized RFID device 16. Based on the RFID tag, the pacer/ICD determines the particular drug and dosage being ingested and compares this information against an on-board database listing drugs currently prescribed to the patient, the prescribed dosages, and the frequency with which the drugs should be taken (i.e. once per day, twice per day, etc.) so as to verify that the correct drug is being taken at the correct dosage level and at the correct frequency. Assuming that is the case, the date/time and drug/dosage of the ingested medication are stored within a database maintained within memory of the pacer/ICD. Otherwise, appropriate warning signals and/or reminder signals are generated. For example, if the patient fails to take a prescribed medication in a timely manner, a reminder signal may be generated to remind the patient. If the patient takes the wrong dosage or takes the wrong medication entirely, a warning signal may be generated to alert the patient. Warning/reminder signals may be generated internally using an implanted warning/reminder device 18, which may be, for example, a vibrating device or a "tickle" voltage warning device providing perceptible stimulation directly to the patient. The warning device may be part of, or contained in, the pacer/ICD itself. Additionally, or in the alternative, warning/reminder signals may be transmitted to a bedside reminder/warning system 22 for display thereon. The bedside monitor may provide audible or visual alarm signals to alert the patient as well as textual or graphic displays.

Figure 12:
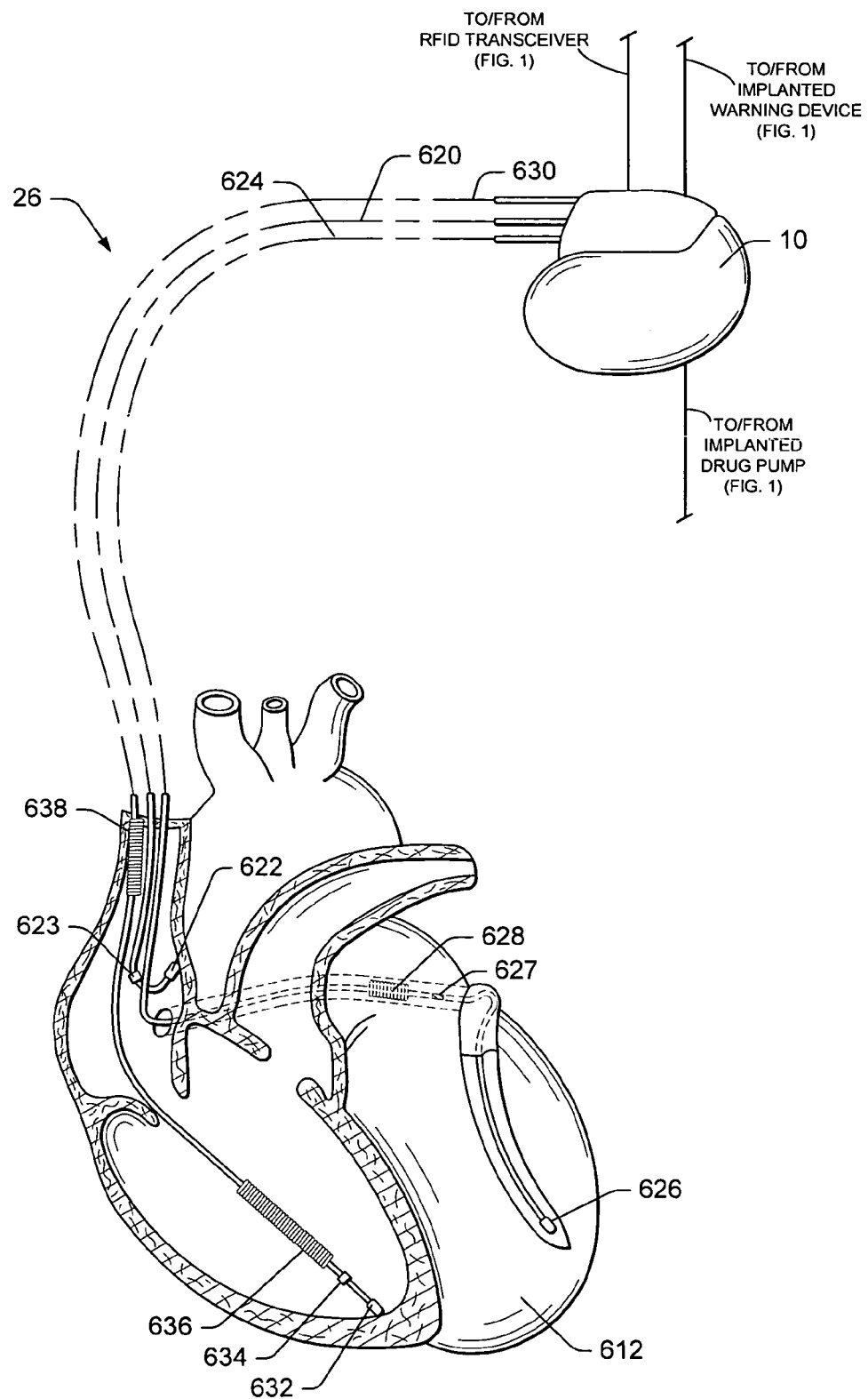
FIG. 12 is a simplified diagram illustrating the pacemaker or ICD of FIG. 1 and its lead system.

Depending upon the particular implementation, the bedside system may also forward any pertinent warning signals to the physician that originally prescribed the medication so as to advise the physician. The warning signals may be relayed via a trans-telephonic system or any other suitable communication system. In addition, if the patient fails to take a critical medication, an implantable drug pump 24 may be employed to deliver a reserve quantity of the medication stored therein to ensure that the patient does not go without the medication for an extended period of time. If the prescribed medication is a heart medication, such as an anti-arrhythmic or anti-thrombolytic medication, the pacer/ICD may also adjust pacing therapy in an attempt to compensate for failure to take the prescribed medication. Pacing therapy is delivered to the heart via a set of implanted leads 26, only two of which are shown in FIG. 1. A full set of leads is illustrated in FIG. 12.

For the invention to be most advantageously exploited, all indigestible prescription medications are preferably provided with miniaturized RFID devices, each encoded with an RFID tag identifying the particular medications contained therein and the dosage. In this manner, any prescription medication being ingested by the patient can be detected and identified. Alternatively, only certain critical medications are equipped with RFID devices, i.e. medications that must be taken in precise dosages in a timely manner to avoid life-threatening conditions.

In other cases, only certain classes of medications are equipped with RFID devices. For example, within the field of cardiac rhythm management, it may be sufficient that pills containing selected heart medications be equipped with RFID devices. In addition, the use of RFID-based technology is merely exemplary. Any suitable technology may be used for transmitting appropriate identification signals from a pill being ingested to an implanted decoding device. An RFID-based example is described herein since RFID technology is well-suited for use with the invention, particularly because RFID-based devices may be miniaturized for attachment to individual tablets, capsules and the like for ingestion.

Thus, FIG. 1 provides an overview of an implantable system for monitoring drug ingestion based on RFID tag signals. Internal signal transmission lines provided for interconnecting the various components of the system are not all shown in the figure. Wireless signal transmission may alternatively be employed, though care should be taken to ensure that any internal wireless transmission signals between implanted components do not interfere with RFID signals. In addition, the particular locations of the implanted components shown in FIG. 1 are merely illustrative and may not necessarily correspond to actual implant locations. As will be explained, in some implementations, the RFID transceiver is preferably positioned as close to the esophagus or stomach as possible.

Note that embodiments may be implemented that do not necessarily incorporate all of the components illustrated in FIG. 1. In many cases, for example, the implanted system will include only the pacer/ICD, its leads and the RFID transceiver, with all warning/reminders transmitted to the bedside system. Drug pumps and internal warning devices are not necessarily implanted. In other embodiments, the implanted system may potentially utilize the leads of the pacer/ICD for detecting RFID tag signals from active RFID devices only, with no separate RFID transceiver provided for detecting RFID tag signals from passive RFID devices. In still other embodiments, the implanted system does not employ a pacer/ICD at all. Other implantable medical devices may instead be configured to perform the RFID-based monitoring techniques of the invention, such as devices provided for stimulating or sensing the nervous system, muscles, glands, organs, or the like.

Alternatively, a dedicated device may be implanted solely for the purpose of performing the RFID-based monitoring techniques of the invention, i.e. a device that does not additionally perform any other implantable medical device functions. An RFID device represents just one type of EID device. Other types of EID devices may instead be employed. An example involving EID devices that transmit signals via biphasic current pulses is described below with reference to FIGS. 14-15.

No attempt is made herein to describe all possible combinations of components that may be provided in accordance with the invention. An example employing a pacer/ICD is described herein since many patients benefiting from the ID-based monitoring techniques of the invention are elderly patients who may also require a pacer/ICD to address heart problems. Hence, by configuring a pacer/ICD to implement the technique of the invention, a single system may be implanted that provides both medication monitoring and cardiac rhythm management.

Figure 2:
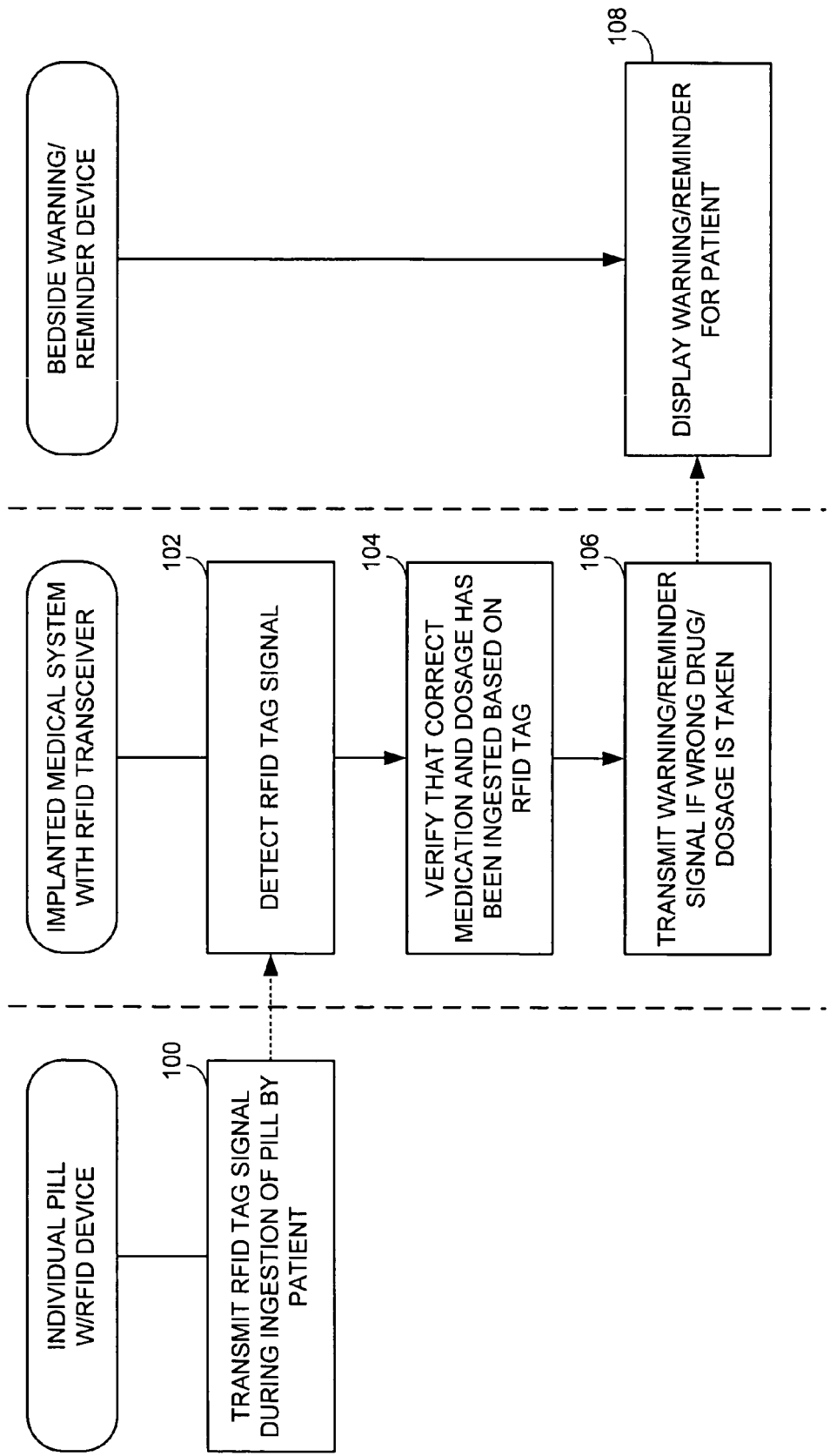
FIG. 2 is a flow chart illustrating, at a high level, an exemplary method for automatically monitoring prescription drug intake, which employs the implantable system of FIG. 1, wherein warning/reminder signals are generated if the correct dosages of prescribed medications are not taken in a timely manner.

Overview of Technique for Monitoring Ingestion of Medications Using an Implanted System The flow chart of FIG. 2 illustrates a general method for monitoring ingestion of prescribed medications using an implantable system. This method may be implemented by the system FIG. 1 or by any other suitable implantable system. In the flow chart of FIG. 2, operations performed by the RFID device of a pill being ingested are shown on the left; operations performed by an implanted medical system are shown in the middle; operations performed by an external bedside warning/reminder device are shown on the right. Briefly, beginning at step 100, an RFID device attached to a pill being ingested transmits an RFID signal as it is being ingested. If the RFID device is passive, the RFID signal is transmitted only in response to a query from the implantable system. If the RFID device is active, the RFID signal is instead transmitted periodically. Particular examples specific to active or passive RFID devices are described below. In any case, the implanted system uses its RFID transceiver to detect the RFID tag signal, at step 102. At step 104, the implanted system then accesses on-board databases to verify that the medication being ingested was prescribed to the patient and to verify that the correct dosage has been taken. Appropriate warning/reminder signals are transmitted, at step 106, from the implanted system to the bedside warning/reminder device, which displays the warning/reminder for the patient, at step 108 and, optionally, forwards the warning/reminder to the prescribing physician via the public switched telephone network (PSTN), the Internet, a wireless communication network, or any other suitable communication network. See, e.g., communication techniques set forth in U.S. Pat. No. 6,249,705, "Distributed Network System for Use with Implantable Medical Devices".

The bedside monitor provides audible alerts along with textual displays. Depending upon the configuration of the bedside monitor, specific textual displays may be generated for describing particular warning/reminders. Some exemplary textual warning/reminders are as follows:

Reminder—The correct dosage of the following prescribed drug has not been taken: PROCAINAMIDE. If you have forgotten to take the prescribed drug, please do so now.

Warning—The following prescribed drug has not been taken: PROCAINAMIDE. It appears that a different drug has been taken instead. Please contact your physician immediately.

Preferably, confirmation messages are displayed whenever the correct drug and dosage has been taken. In that way, if neither a confirmation message nor a warning message is displayed following ingestion of a pill equipped with an RFID device, the patient is thereby alerted that the monitoring system may not be functioning properly. Each patient having an implanted device capable of detecting RFID-equipped pills is preferably provided with a bedside monitor for installation at his or her home. Additionally, bedside monitors are preferably provided in clinics, hospitals, and the like.

The verification procedure performed at step 104 preferably utilizes a set of databases stored within onboard memory of the implanted system. Exemplary databases are illustrated in FIG. 3. A first database 110 provides information relating individual prescription drugs to the unique RFID tags associated therewith. A second database 112 lists particular medications that have been prescribed to the patient along with the prescribed dosage and the prescribed frequency, i.e. "once per day", "twice per day", etc. A third database 114 provides a record of drugs already ingested, the dosage, and the date/time the drug was taken. In one example, each RFID tag is a unique 96-bit tag, which identifies, at minimum, the medication and its dosage. Other data tag sizes may instead be employed. The length of the data tag to be used may depend on the total number of unique drug/dosage combinations of pills expected to be equipped with RFID tags. If relatively few pills are to be equipped with RFID tags, then relatively short RFID tags may be sufficient to uniquely distinguish one from the other. If a large number of different pills are to be equipped with RFID tags, then longer RFID tags may be needed to uniquely distinguish one from the other. Alternatively, each RFID tag may be specific so as to be long enough to additionally encode a unique serial number identifying the particular pill and its manufacturer for tracking purposes.

The verification procedure performed at step 104 preferably utilizes a set of databases stored within onboard memory of the implanted system. Exemplary databases are illustrated in FIG. 3. A first database 110 provides information relating individual prescription drugs to the unique RFID tags associated therewith. A second database 112 lists particular medications that have been prescribed to the patient along with the prescribed dosage and the prescribed frequency, i.e. "once per day", "twice per day", etc. A third database 114 provides a record of drugs already ingested, the dosage, and the date/time the drug was taken. In one example, each RFID tag is a unique 96-bit tag, which identifies, at minimum, the medication and its dosage. Other data tag sizes may instead be employed. The length of the data tag to be used may depend on the total number of unique drug/dosage combinations of pills expected to be equipped with RFID tags. If relatively few pills are to be equipped with RFID tags, then relatively short RFID tags may be sufficient to uniquely distinguished one from the other. If a large number of different pills are to be equipped with RFID tags, then longer RFID tags may be needed to uniquely distinguish one from the other. Alternatively, each RFID tag may be specific so as to be long enough to additionally encode a unique serial number identifying the particular pill and its manufacturer for tracking purposes.

To identify a particular pill being ingested, the implanted system compares the RFID tag received from the RFID device of the pill against prescription drug/RFID tag database 110. In the example of FIG. 3, database 110 lists various exemplary dosages of procainamide and diltiazem, which are anti-arrhythmic heart medications. If, for example, the RFID tag received from the pill being ingested matches the tag associated with the 375 mg capsule of procainamide, the implanted system thereby determines that the patient has taken 375 mg of procainamide and records that information along with the date/time within the medication intake record database 114. The system then accesses the patient prescription database 112 to determine whether that particular medication and dosage had been prescribed to the patient. If not, a suitable warning signal is generated. Periodically, the implanted system also examines the patient prescription database to identify any medications that had been prescribed, but which the patient has not taken within an expected time frame determined by the prescribed frequency. In this manner, the system can generate reminder signals for reminding the patient to take the prescribed medication. This will be described in greater detail below with reference to FIG. 7.

In one example, database 110 only lists those medications that have been prescribed the patient. This minimizes the amount of data to be stored within the database. If the RFID tag received from a pill being ingested does not match any of the entries within the database, the implanted system generates a warning signal indicating that an "unknown" medication has been ingested. Alternatively, database 110 may additionally include RFID tags for any and all medications equipped with RFID devices so that the implanted system can identify the particular medication that had been erroneously ingested. This allows the physician, once notified, to evaluate any adverse consequences to the patient and, in particular, to identify any possible drug interaction problems with other medications that the patient might be taking. However, a greater amount of device memory is required. In still other implementations, the database stores RFID tags for all drugs within certain classes of medications. For example, if the implanted system is a pacer/ICD, the database may store RFID tags for all heart medications. If the implanted system is instead a system for stimulating portions of the nervous system, RFID tags for all drugs directed to treating the nervous system may instead be stored. In any case, the list of drugs to be stored within database 110 may be recorded therein during device manufacture, following device implant via a device programmer, or during a subsequent follow-up session between patient and physician (again via a device programmer.)

The list of drugs within database 112 is updated using a device programmer whenever the physician prescribes new drugs to the patient, changes to the prescribed dosage or frequency, or withdraws any previous prescriptions. In this manner, database 112 is kept up-to-date. If desired, pharmacists may be provided with suitable devices for transferring prescription data into the implanted system of a patient so that, whenever a patient picks up a new prescription, the pharmacist can update the data stored within the implanted device to reflect that prescription. Coordination of prescription information by pharmacists via RFID devices mounted to pill vials is discussed in U.S. Pat. No. 5,963,136 to O'Brien entitled "Interactive Prescription Compliance and Life Safety System." However, there is no mention therein of mounting RFID devices to the pills themselves for ingestion or of the use of an implantable system for detecting the RFID-equipped pills.

Alternatively, rather than maintaining the databases of FIG. 3 within the implanted device itself, the databases are instead maintained within the bedside monitor system. Within such an implementation, the implanted system merely forwards RFID tags received from pills being ingested to the bedside monitor, which then accesses the databases stored therein to verify that the correct prescription drug has been taken and to issue any appropriate warning or reminder. This reduces the memory and processing requirements of implanted device itself. Assuming the implanted system is in communication with the bedside monitor at the time the drug is ingested, the RFID tag is immediately relayed to the bedside monitor so that a warning signal, if needed, may be promptly generated. If not, transmission of the RFID tag is deferred until the next time the implanted system is in communication with the bedside monitor. In yet another implementation, if no bedside monitor is provided, RFID tags for ingested medication are merely stored within the implanted system until a follow-up session between patient and physician. At that time, the physician transfers the RFID tags from the implanted system to the external programmer (along with other stored diagnostic information) for display thereon. The physician can then verify that the patient has been properly taking prescribed medications. An implementation wherein the databases are maintained within the implanted device itself is preferred since it allows therapy (such as pacing therapy) to be immediately adjusted to compensate for failure to take prescribed drugs in a timely manner. In addition, assuming an internal warning system is employed, warning/reminder signals may be immediately provided to the patient. Otherwise, warning/reminder signals can only be provided to the patient after the implanted system has relayed data to the bedside monitor or some other external system, which may result in a substantial delay.

Also, although primarily described with respect to detecting the ingestion of prescription medications in pill form, the techniques of the invention described herein are also applicable to detection of ingestion of non-prescription drugs in pill form, as well as other products provided in pill form, such as dietary supplements. The techniques of the invention are also applicable to the detection of the ingestion of other items or products besides pills, such as quantities of liquid medication to be taken orally. For example, a single dosage of medication in liquid form may be provided with an RFID device floating therein (properly encapsulated), which is then ingested by the patient while he or she drinks the medication.

Figure 4:
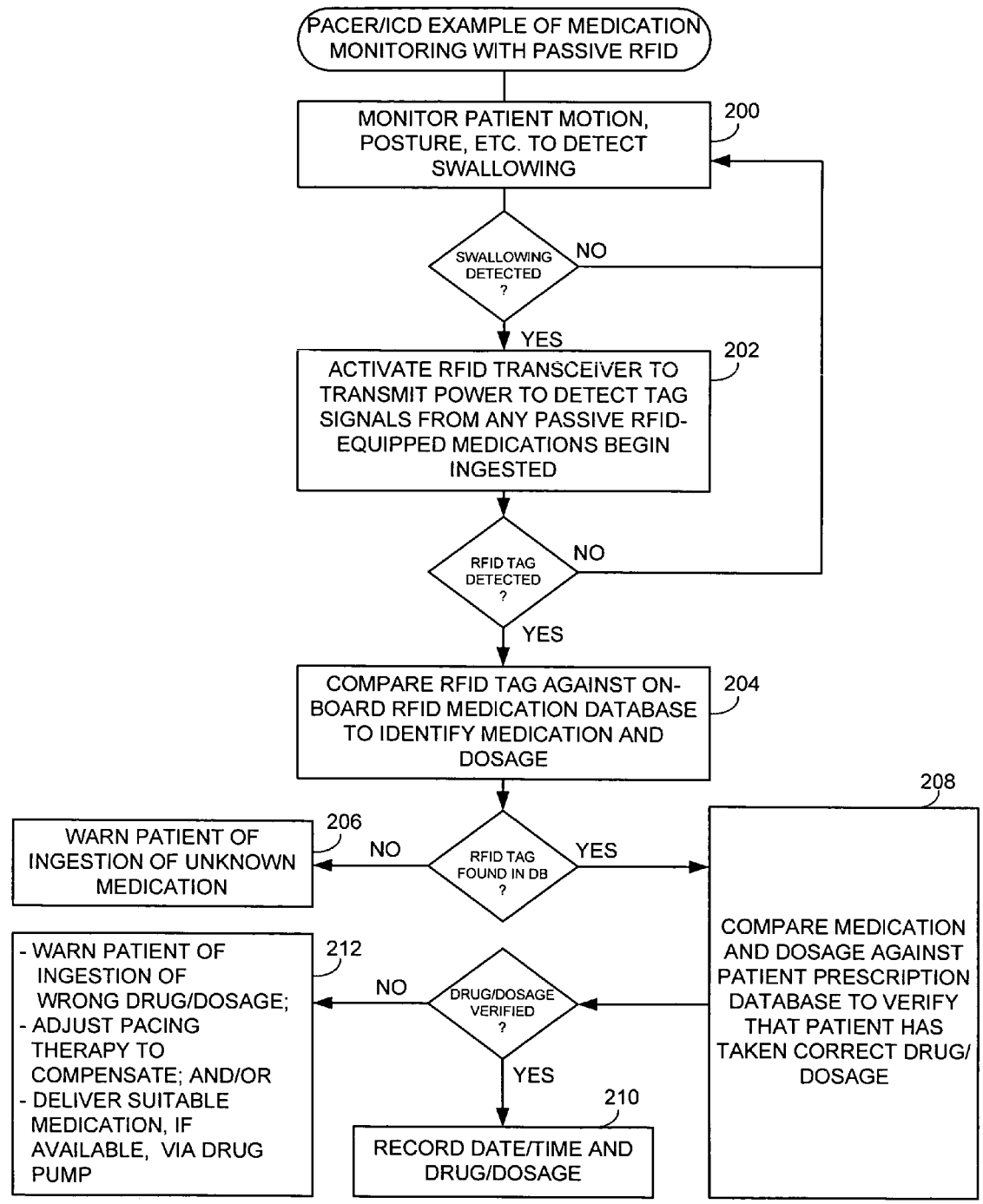
FIG. 4 is a flow chart illustrating an exemplary technique for use with the system of FIG. 1 for detecting intake of pills equipped with passive RFID devices.

1. Exemplary Technique for Monitoring Ingestion of Medications Using Passive RFID FIG. 4 illustrates an exemplary technique for monitoring medication intake via pills equipped with passive RFID devices, particularly for use with a pacer/ICD. Briefly, to reduce power consumption within the pacer/ICD, the pacer/ICD seeks to detect when the patient is swallowing and only outputs RFID power signals at such times. Also, with the technique of FIG. 4, in addition to generating warning/reminder signals, the technique adjusts pacing therapy to compensate for failure to take prescribed medications and/or activates an implanted drug pumped to deliver suitable alternate medications, if available.

Beginning at step 200, the pacer/ICD monitors patient motion, posture, etc. to detect when the patient is swallowing. This will be described more thoroughly with reference to FIG. 5. Assuming the patient is swallowing, and hence might possibly be swallowing a pill provided with a passive RFID device, the pacer/ICD, at step 202, activates an RFID power transmission antenna to transmit power, preferably toward the esophagus and stomach of the patient. In one example, the power transmission antenna is activated for 15 seconds. If the patient was indeed swallowing a pill equipped with a passive RFID device, the circuitry of the pill uses the power received from the pacer/ICD to transmit its encoded RFID tag, which the antenna of the pacer/ICD then detects. In this regard, the passive RFID device is a so-called "full-duplex" transponder, i.e. an RFID device that transmits the RFID tag concurrently as it receives power. Alternately, the RFID device may be a "half-duplex" transponder, i.e. an RFID device that stores received power, then transmits the RFID tag shortly thereafter. Full-duplex is preferred as it reduces the number of circuit components required on the RFID device.

An RFID device with full-duplex circuit components will be described below with reference to FIG. 10. Of course, most of the time that the patient is swallowing, he or she will merely be ingesting food or beverage and will not be ingesting an RFID-equipped pill. Hence, no RFID tag signal will be detected by the pacer/ICD at that time. Nevertheless, by activating the power transmission antenna of the pacer/ICD only while the patient is swallowing, substantial power savings can be achieved as compared to a system that would otherwise transmit power at all times.

Low-frequency RFID signals are preferably employed, e.g. signals operating at about 125 kHz. By using low-frequency signals, the signals can properly propagate through the tissues of the body. However, lower frequencies require generally larger device components and so frequencies below 125 kHz are not preferable. The transmission power of the pacer/ICD and the return transmission power of the RFID device of the pill are preferably set to the lowest power levels sufficient to ensure that the RFID tag of a pill being ingested will be properly detected by the pacer/ICD. This helps reduce power consumption by the pacer/ICD as well as reduce the risk that the pacer/ICD may inadvertently detect the RFID tag of a pill external to the body, perhaps a pill that the patient intends to ingest but then forgets to ingest. Optimal transmission power values to be used depend upon the size, shape and orientation of the antenna of the pacer/ICD, its proximity to the esophagus and stomach, and characteristics of the intervening tissues, as well as the characteristics of the RFID device of the pill. Routine experimentation may be performed to identify optimal power transmission levels based upon these parameters. Otherwise routine experimentation may be employed to determine appropriate power transmission levels for the antenna of the pacer/ICD as well as appropriate power transmission levels for the RFID device of the pill. Routine experimentation may also be employed to determine optimal parameters for the size, shape, position and orientation of the antenna of the pacer/ICD. Preferably, following implant of the pacer/ICD, a physician or other medical professional performs tests to determine the optimal power level sufficient to ensure reliable detection of pills being ingested by the particular patient in which the pacer/ICD has been implanted. The pacer/ICD is then programmed to use the optimal power level. The power level may be increased during a follow-up session if the patient complains that the pacer/ICD has failed to detect medications properly ingested.

Assuming that an RFID tag has been detected then, at step 204, internal components of pacer/ICD compare the RFID tag against the on-board prescription drug/RFID tag database (i.e. database 110 of FIG. 3) to determine if it corresponds with any prescription drugs listed therein. If not then, at step 206, a warning is issued indicating that the patient has ingested an unknown medication, which has not been prescribed to the patient. Assuming, however, that the RFID tag is found within the database, then at step 208, the pacer/ICD compares the medication and dosage of the pill against the on-board patient prescription database (i.e. database 112 of FIG. 3) to verify that the correct drug/dosage as been ingested, and within a proper time frame. If so then, at step 210, the pacer/ICD records the date/time and drug/dosage in the intake record database (i.e. database 114 of FIG. 3). If not, then, at step 212, the pacer/ICD: warns the patient of ingestion of the wrong drug or wrong dosage; automatically adjusts pacing therapy in attempt to compensate for failure to take the correct drug/dosage; and/or controls an implantable drug pump to deliver a reserve quantity of the prescribed medication or an alternate acceptable medication, if available.

Generation of warning signals is discussed above. Insofar as control of therapy is concerned, the pacer/ICD may adjust pacing control parameters (subject to programming commands previously provided by the physician) in attempt to compensate for failure to take the prescribed drug or failure to take the correct dosage of the prescribed drug. In one example, should the patient fail to take medications intended to reduce the risk of episodes of AF, the pacer/ICD may be programmed to automatically activate atrial overdrive pacing to compensate. (Overdrive pacing of the atria has been found to be effective in reducing the risk of AF.) Alternatively, if overdrive pacing is already active, the pacer/ICD may increase the aggressiveness overdrive pacing. A particularly effective overdrive pacing technique for suppressing AF, referred to as dynamic atrial overdrive (DAO) pacing, is described in U.S. Pat. No. 6,519,493 to Florio et al. See also: U.S. Patent Application 2003/0130704, also of Florio et al., entitled "Method and Apparatus for Dynamically Adjusting a Non-Linear Overdrive Pacing Response Function", filed Jan. 9, 2002; and U.S. Patent Application 2003/0130703, of Florio et al., entitled "Method And Apparatus For Dynamically Adjusting Overdrive Pacing Parameters", filed Jan. 9, 2002.

In another example, should the patient fail to take antithrombolytic drugs intended to reduce the risk of a thrombosis (i.e. a blood clot), the pacer/ICD automatically reduces pacing rates or deactivates overdrive pacing, in an attempt to reduce the likelihood of a thrombosis. In yet another example, should the patient fail to take medications intended to reduce the severity of heart failure, the pacer/ICD may automatically activate cardiac resynchronization therapy (CRT) in an attempt to improve heart function. Exemplary heart failure medications include ACE inhibitors, diuretics, digitalis and compounds such as captopril, enalapril, lisinopril and quinapril. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing". In still another example, if the implanted system is an ICD and the patient has failed to take drugs prescribed to reduce the risk of an episode of VF, the pacer/ICD may be programmed to immediately charge defibrillation capacitors. In this manner, should an episode of VF occur, the pacer/ICD would be able to immediately deliver a defibrillation shock, thereby increasing the chances of patient survival.

These are merely a few examples pertaining to heart conditions, which are particularly useful for implementations employing a pacer/ICD. In general, a wide variety of pacing and defibrillation control parameters may potentially be selected by the physician for automatic control based upon detection of failure to take prescribed medications. For other types of implantable medical devices, such as devices that stimulate the nervous system, control parameters specific to those devices may be automatically adjusted in response to failure to take prescribed medications. The particular control parameters to be automatically adjusted and the form of adjustment depends upon the functionality of the implanted device, the prescribed medications and the consequences to the patient of failure to take the prescribed medications. Those skilled in the art may make those determinations for particular medications and for use with particular implanted devices.

Insofar as the automatic control of an implanted drug pump is concerned, a drug pump may be provided with a quantity of critical medication such that, should the patient fail to take medication (perhaps because he or she has run out of the oral form of the medication or is incapacitated and cannot take the medication orally), the drug pump may provide a reserve quantity of the drug to ensure that the patient at least receives some of the drug. Depending upon the particular medication, alternative compounds may be required for delivery via an implantable drug pump. Routine experimentation may be employed to identify alternate medications that are safe and effective for use in connection with an implantable drug pump, Implantable drug pumps are discussed in U.S. Pat. No. 5,328,460 to Lord, et al., entitled "Implantable Medication Infusion Pump Including Self-Contained Acoustic Fault Detection Apparatus".

For implementations wherein the implanted system is a pacer/ICD and the prescribed medications are heart medications, techniques for automatically evaluating the efficacy of medications based upon examination of internal electrical cardiac signals may be employed in conjunction with the techniques of the present invention. See, in particular, U.S. patent application Ser. No. 10/608,409, of Boileau et al., entitled "Method and Apparatus for Monitoring Drug Effects on Cardiac Electrical Signals Using an Implantable Cardiac Stimulation Device", filed Jun. 26, 2003, which is incorporated by reference herein. Using techniques described in that application, the pacer/ICD may be programmed to automatically detect changes, if any, within the electrical cardiac signals caused by failure to take the prescribed medication. The pacer/ICD preferably postpones any changes to pacing control parameters that would otherwise be triggered by failure to take the prescribed medication until a reduction in efficacy becomes apparent based upon an examination of the cardiac signals. In this manner, the pacer/ICD avoids making any unnecessary changes to control parameters if there is still sufficient medication within the patient's system to benefit the patient In addition, an examination of drug efficacy based on cardiac signals serves to confirm an RFID-based detection of failure to take prescribed medications. Circumstances may arise, for example, where the pacer/ICD fails to detect the RFID tag of a medication that has been properly ingested, perhaps due to a failure of the RFID device of the pill itself. In such circumstances, the pacer/ICD might unnecessarily adjust pacing control parameters. By deferring any such adjustments until confirmation is provided based upon a drug efficacy analysis, unnecessary adjustments are avoided.

Figure 5:
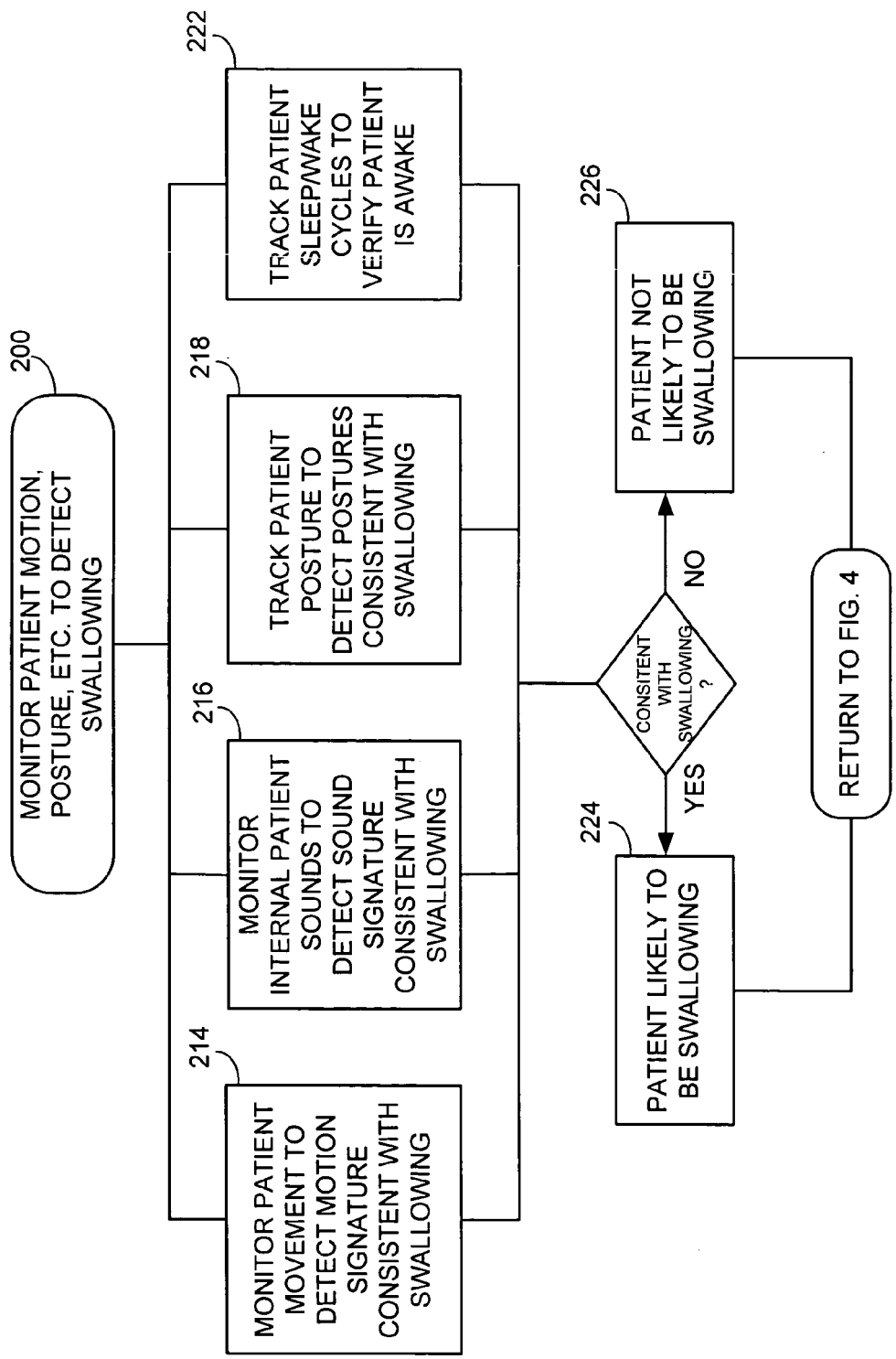
FIG. 5 is a flow chart illustrating an exemplary method for use with the technique of FIG. 1 for determining when the patient is in the act of swallowing for use in triggering a passive RFID device.

Referring now to FIG. 5, techniques will now be described for detecting when the patient is in the act of swallowing, for use at step 200 of FIG. 4. To detect swallowing, the pacer/ICD simultaneously monitors a number of patient parameters including patient motion, patient posture, internal patient sounds, and patient sleep/wake cycles. At step 214, for example, the pacer/ICD employs an accelerometer or other motion detection device to monitor patient movement to identify a motion signature consistent with swallowing. In this regard, slight patient movements and vibrations occurring while swallowing, particularly while swallowing a relatively large pill, are distinct from other patient movements. The pacer/ICD stores a motion signature template indicative of movement occurring during swallowing a pill within onboard memory and compares patient movements detected by the accelerometer against the template to identify circumstances wherein it appears likely that the patient is swallowing a pill. Otherwise conventional pattern matching techniques may be employed. In one example, following device implant, the patient is asked to swallow one or two pills during which time the pacer/ICD is programmed to detect resulting motions and generate a motion signature for subsequent use. Alternatively, a generalized signature applicable to a wide population of patients may instead be employed. In any case, following step 214, the pacer/ICD generates a value indicating whether it appears the patient is swallowing a pill or not. Depending upon the implementation, this value may be used alone or in combination with corroborating parameters for use in activating the RFID device of the pacer/ICD to search for passive RFID tags. In the example of FIG. 5, corroboration is provided based upon patient posture, internal patient sounds, and patient sleep/wake cycles.

Simultaneously, or alternatively, at step 216, the pacer/ICD employs an acoustic sensor to monitor internal patient sounds (i.e. auscultations) to identify a sound signature consistent with swallowing. As with movement, internal patient sounds occurring while swallowing,. particularly while swallowing a relatively large pill, are generally distinct from other internal patient sounds. The pacer/ICD stores a sound signature template indicative of internal patient sounds occurring while swallowing a pill and compares internal patient sounds against the template to identify circumstances wherein it appears likely that the patient is swallowing a pill. As with movement-based detection, the patient is preferably asked to swallow one or more pills following the device implant during which time the pacer/ICD detects resulting internal sounds and generates a sound signature for subsequent use. Alternatively, a generalized sound signature applicable to a wide population of patients may instead be employed. Acoustic sensors for use with pacer/ICDs for detecting heart sounds may be adapted for use in detecting sounds associated with swallowing. See, for example, U.S. Pat. Nos. 5,836,987, 5,935,081, 6,477,406 and 6,527,729. Following step 216, the pacer/ICD generates a value indicating whether it appears the patient is swallowing a large pill or not. Depending upon the implementation, this value may be used alone or in combination with patient motion or other corroborating parameters for activating the RFID device.

At step 218, the pacer/ICD tracks patient posture to determine whether posture is consistent with, or inconsistent with, the act of swallowing a pill. If inconsistent, then a detection of swallowing made based upon patient movement or internal sounds is ignored. For example, pills are rarely, if ever, swallowed while the patient is prone (i.e. while the patient lies on his or her stomach). Accordingly, if an analysis of posture concludes that patient is prone, the RFID antenna of the pacer/ICD is not activated to transmit power. Techniques for detecting patient posture and/or changes in posture are set forth in U.S. patent application Ser. No. 10/329,233, of Koh et a/., entitled "System and Method for Determining Patient Posture Based On 3-D Trajectory Using an Implantable Medical Device", filed Dec. 23, 2002, which is incorporated by reference herein.

At step 220, the pacer/ICD tracks patient sleep/wake cycles to verify that the patient is awake. If asleep, then a detection of swallowing made based upon patient movement or internal sounds is likewise ignored. Examples of sleep detection techniques are set forth in the following patents or patent applications: U.S. Pat. No. 5,476,483, to Bornzin et al., entitled "System and Method for Modulating the Base Rate During Sleep for a Rate-responsive Cardiac Pacemaker"; U.S. Pat. No. 6,128,534 to Park et al., entitled "Implantable Cardiac Stimulation Device And Method For Varying Pacing Parameters To Mimic Circadian Cycles"; and in patent application Ser. No. 10/339,989, to Koh et al., entitled "System and Method for Detecting Circadian States Using an Implantable Medical Device", filed Jan. 10, 2003.

If an analysis of patient motion, internal patient sounds, patient posture and patient sleep/wake cycles indicates the patient is swallowing, appropriate internal flags or signals are generated at step 222. Otherwise, converse flags or signals are generated at step 224. In any case, processing returns to FIG. 4 wherein, if the patient is found to be swallowing, the antenna of pacer/ICD is activated to transmit power.

2. Exemplary Technique for Monitoring Ingestion of Medications

Using Active RFID

Figure 6:
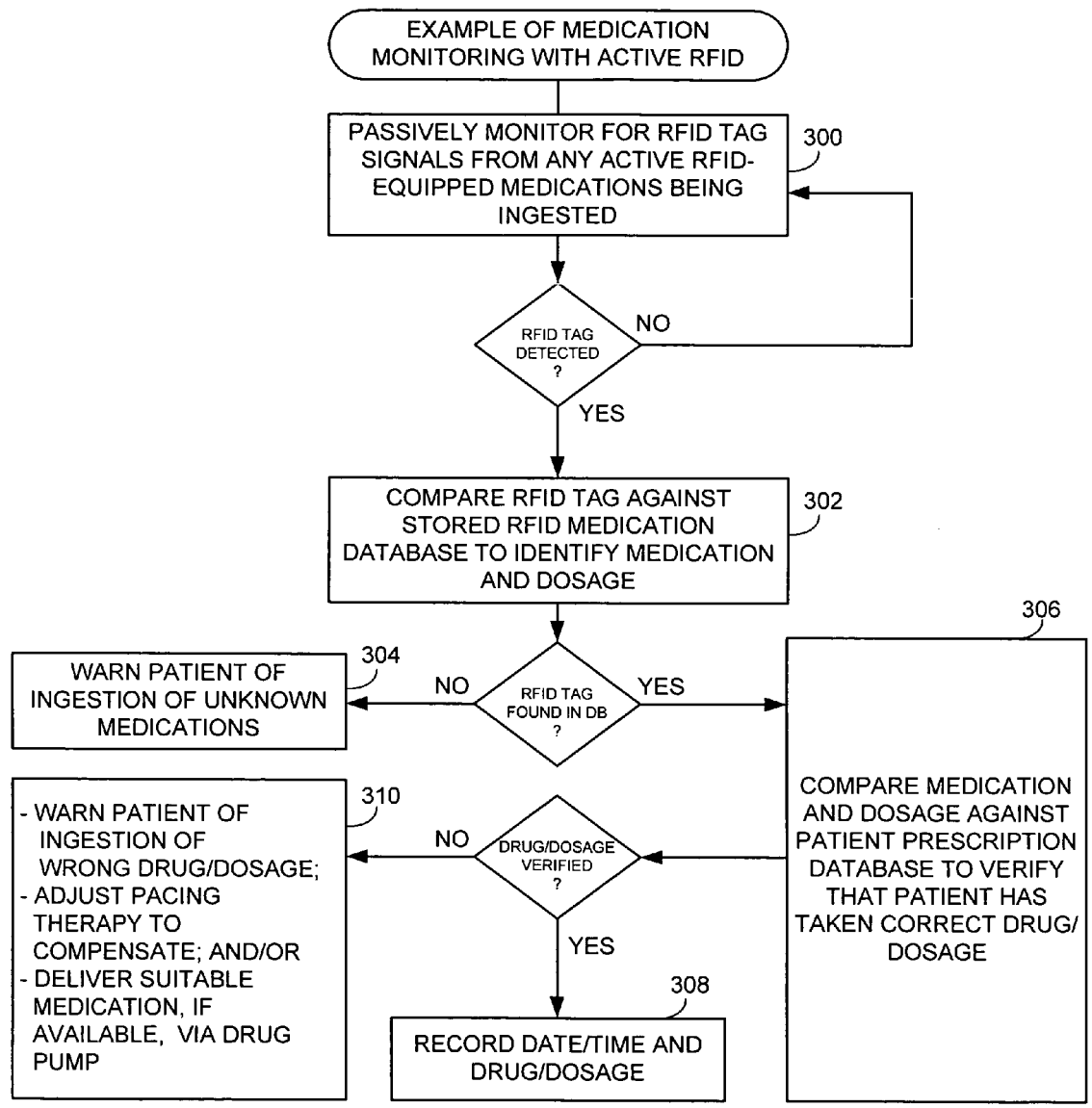
FIG. 6 is a flow chart illustrating an exemplary technique for use with the system of FIG. 1 for detecting intake of pills equipped with active RFID devices.

FIG. 6 illustrates an exemplary technique for monitoring medication intake via pills equipped with active RFID devices, particularly for use with a pacer/ICD. Many of the techniques of FIG. 6 are similar to those of FIG. 4 and only pertinent differences will be described in detail. In particular, whereas substantial power savings may be achieved within the technique FIG. 6 by limiting the search for passive RFID devices to only those periods of time when the patient is swallowing, detection of active RFID devices is far less power intensive (at least for the pacer/ICD) and hence, in this example, the detection techniques of FIG. 5 are not employed. Beginning at step 300, the pacer/ICD passively monitors, via a transceiver or a receiver, for any active RFID signals generated by pills being swallowed. Circuit components for performing these functions will be described below with reference to FIGS. 10-11.

Again, preferably, low frequency RFID signals are used to allow the signals to propagate through the tissues of the body. The transmission power of the RFID device of the pill is preferably set to the lowest power level sufficient to ensure that the RFID tag of a pill being ingested will be properly detected by the pacer/ICD. This helps reduce power consumption by the RFID device of the pill as well as reduce the risk of false detections based on RFID pills held outside the body but not ingested. Optimal power values to be used depend upon the size, shape and orientation of the leads or antennas of the pacer/ICD, their proximity to the esophagus and stomach, and the characteristics of the intervening tissues, as well as the characteristics of the sensing circuitry of the pacer/ICD. Routine experimentation may be performed to identify optimal power levels based upon these parameters. Otherwise routine experimentation may be employed to determine appraise power transmission levels for the active RFID device of the pill. Preferably, following implant of the pacer/ICD, the physician performs tests to determine the optimal sensitivity level for use with the pacer/ICD sufficient to ensure reliable detection of active RFID signals from pills being ingested by the particular patient in which the pacer/ICD has been implanted. The pacer/ICD is then programmed to use the optimal sensitivity level. The sensitivity level may be adjusted during a follow-up session if the patient complains that the pacer/ICD has failed to detect medications properly ingested or if the pacer/ICD detects pills that were not ingested but merely held in proximity to the body.

Assuming that an RFID tag has been detected, then processing proceeds substantially as before. Briefly, at step 302, the pacer/ICD compares the RFID tag against the on-board prescription drug/RFID tag database to determine if it corresponds with any prescription drugs listed therein. If not, a warning is issued at step 304 indicating that the patient has ingested an unknown medication, which has not been prescribed to the patient. Assuming that the RFID tag is found within the database, then at step 306, the pacer/ICD compares the medication and dosage of the pill against the on-board patient prescription database to verify that the correct drug/dosage as been ingested. If so then, at step 308, the pacer/ICD records the date/time and drug/dosage in the intake record database. If not, then, at step 310, the pacer/ICD warns the patient of ingestion of the wrong drug or wrong dosage, automatically adjusts pacing therapy, and/or controls an implantable drug pump to deliver a reserve quantity of the prescribed medication or an alternate acceptable medication, if available, using techniques already described.

Thus, FIGS. 4-5 illustrate an exemplary passive RFID-based technique, whereas FIG. 6 illustrates an exemplary active RFID-based technique. Preferably, the pacer/ICD is equipped and configured so as to detect either passive or active RFID tag signals. In other words, the pacer/ICD passively monitors for any active RFID signals that may be received from a pill being ingested and, at least while the patient is found to be swallowing, actively transmits low-frequency RFID power signals to detect any passive RFID tags. In this manner, the pacer/ICD may be used in conjunction with either passive or active RFID-equipped prescription medications.

3. Exemplary Technique for Detecting Failure to Ingest Medications

Figure 7:
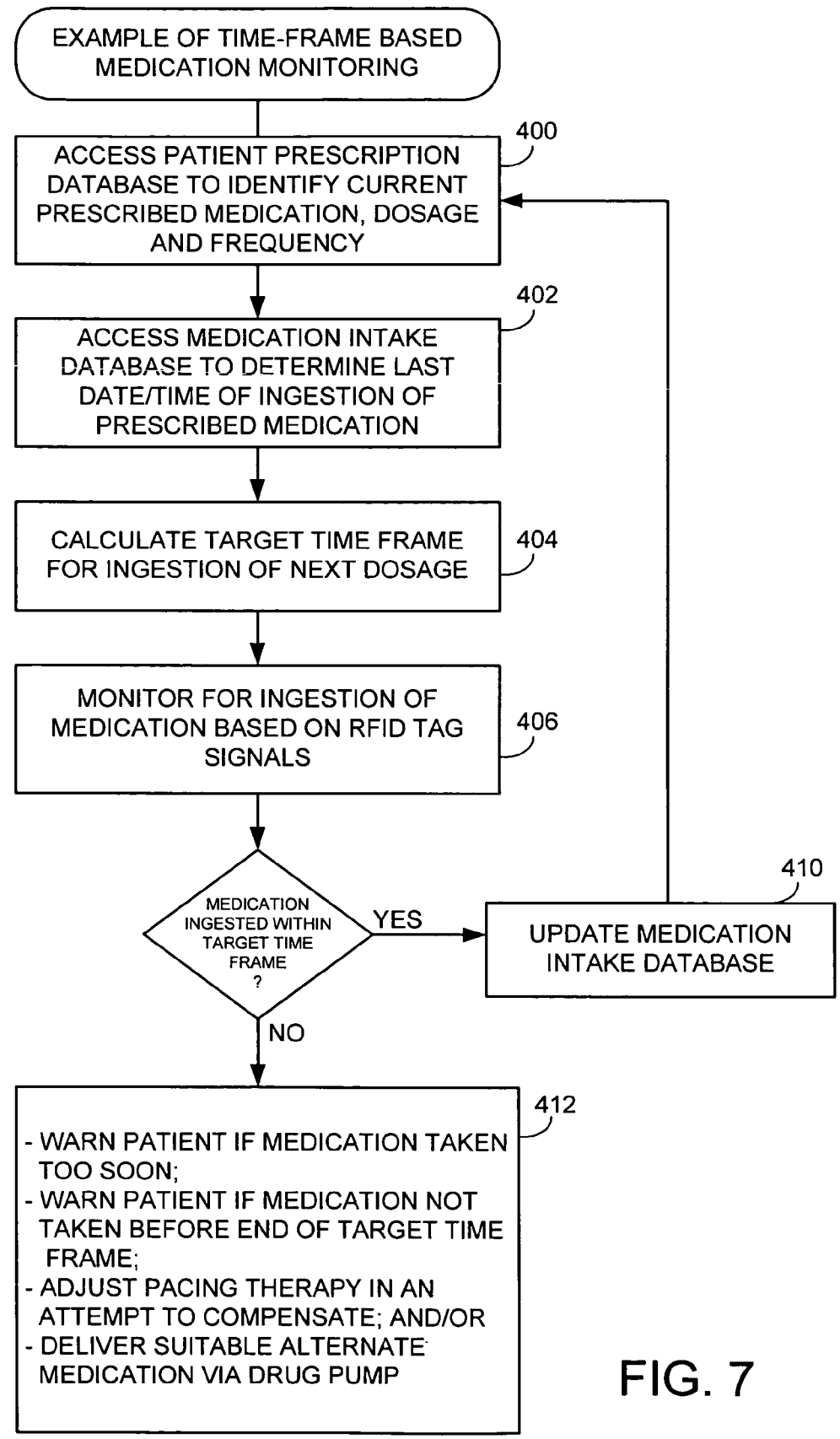
FIG. 7 is a flow chart illustrating an exemplary technique for use with the system of FIG. 1 for detecting if the patient has failed to take a prescribed medication within an expected time frame.

Turning now to FIG. 7, an exemplary technique for determining whether a patient has failed to take a prescribed drug in a timely manner will now be described. This technique is used in conjunction with either or both of the aforementioned techniques. In other words, the pacer/ICD operates to determine whether a pill being ingested has in fact been prescribed using the techniques of FIGS. 4-6 and simultaneously operates to identify circumstances wherein a prescribed pill has not been ingested within an expected time frame using the technique of FIG. 7.

Beginning at step 400, the pacer/ICD periodically accesses the patient prescription database (database 112 of FIG. 3) to identify any currently prescribed medications and to read out the corresponding dosages and frequencies. At step 402, the pacer/ICD then accesses the medication intake record database (database 114 of FIG. 3) to determine the last date and time that each prescribed medication had been ingested. At step 404, a target time frame for ingestion of the next dosage of medication is calculated so that, if patient fails to take a prescribed medication within the target time frame, an appropriate reminder or warning signal may be issued. In this regard, if the patient takes the next dosage too soon (i.e. before the beginning of the target time frame), a warning signal may be issued to that effect. If the patient does not take the next dosage before the end of the target time frame, a reminder signal may be issued and, if necessary, therapy may be adjusted to compensate for failure to take medication.

The determination of the target time frame for a particular prescribed medication is made based upon the prescribed frequency for that medication and the last date/time, if any, that the medication had been ingested. In one example, if the prescribed intake frequency for a particular drug is "once per day", the target time frame for next ingestion is calculated to begin 18 hours following the last recorded ingestion and to extend until 30 hours following the last recorded ingestion. In other words, a 12 hour time frame for ingestion of the next dosage is defined, which is centered 24 hours following the last reported ingestion of the medication. In another example, if the prescribed intake frequency for a particular drug is "twice per day", the target time frame for ingestion of the next dosage begins eight hours following the last recorded ingestion and extends until 16 hours following that last recorded ingestion. Hence, an eight-hour timeframe is defined, centered 12 hours following the last reported ingestion of the medication. These are merely examples. Depending upon the particular implementation, the time frame may be adjusted so as to exclude periods of time when the patient is expected to be asleep. In other words, if the initially-calculated time frame for ingestion of the next dosage would require the patient to take the drug during the middle of the night, the time frame may be adjusted so that warning/reminder signals are not generated while the patient is asleep (unless the drug is so critical that the patient should be awoken during the night to take the medication.)

Then, at step 406, the pacer/ICD monitors for ingestion of medication based upon the RFID tag signals using the techniques discussed above. Assuming the medication is ingested within the target time frame, the pacer/ICD merely updates the medication intake record database, at step 410, and returns to step 400 to calculate the next target time frame for that medication. If, however, the medication was not taken within the target time frame, then step 412 is instead performed wherein the pacer/ICD: generates a warning signal indicating the medication was taken too soon; generates a reminder signals indicating that the medication was not taken within the target time frame; adjusts pacing therapy in attempt to compensate; and/or delivers a suitable alternate medication via an implanted drug pump, if so equipped.

Thus, FIG. 7 illustrates a technique for detecting if a patient has failed to take prescribed medication in a timely manner or if the patient has taken the prescribed medication too soon. The steps of the FIG. 7 are preferably performed periodically, e.g. at least once per hour, or more frequently, particularly if medications have been prescribed that require dosages that are more frequent.

RFID-Equipped Medications

Figure 8:
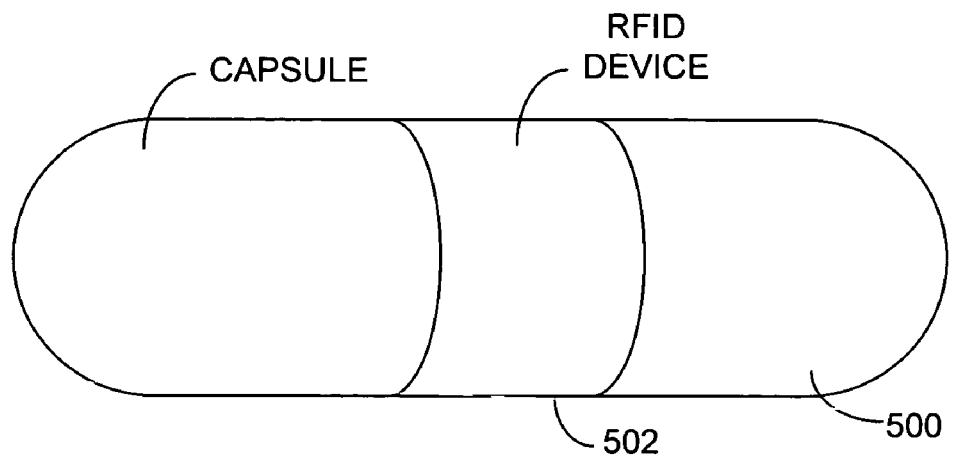
FIG. 8 is a stylized diagram illustrating an individual medication capsule equipped with an RFID device for use with the system of FIG. 1.
Figure 9:
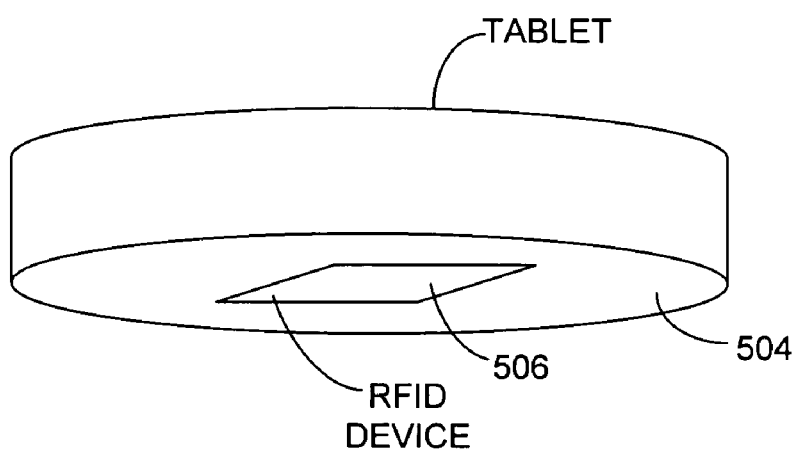
FIG. 9 is a stylized diagram illustrating an individual medication tablet equipped with an RFID device for use with the system of FIG. 1.

Turning now to FIGS. 8-11, RFID-equipped medications will now be described in greater detail. FIG. 8 illustrates an exemplary gel capsule 500 with an RFID device 502 attached thereto. Individual circuits of the RFID device are not shown. As can be seen, the RFID device is wrapped around the perimeter of the capsule. Hence, in this implementation, circuitry of the RFID device may need to be mounted on a flexible substrate to permit it to conform to the curvature of the capsule. However, if the RFID device is sufficiently small relative to the capsule, then a flexible substrate is not required. To affix the RFID device to the capsule, a gel layer (not shown) may be formed around the entire capsule/RFID assembly. The gel layer not only holds the RFID device against the capsule but also protects the device from damage or deterioration and also ensures that the capsule will be easily swallowable by the patient. Note that, if the capsule is a gel capsule normally provided with an outer skin, the RFID device may simply be placed within the outer skin, thus eliminating the need to provide a separate gel layer specifically for enclosing the RFID device. Alternative techniques may be employed for fixing the device to the capsule. FIG. 9 illustrates an exemplary tablet 504 with an RFID device 506 affixed to a flat side surface thereof. Again, an external gel layer (not shown) may be provided around the entire tablet/RFID assembly for the affixing the device to the tablet. Other techniques for affixing the RFID device to the tablet may alternatively be employed.

Alternatively, the RFID device may be enclosed within the pill itself, i.e., during manufacture, the pill is formed around the RFID device. This eliminates the need to affix the RFID device to an external surface of the pill. However, affixing the device to the outside of the pill is preferred for several reasons. With the device attached to the outside of the pill, fabrication techniques for manufacturing the pill need not be modified to account for the device. Instead, the device is merely attached after pill manufacture. Moreover, with the RFID device on the outside surface of the pill, the pill can be easily inspected to verify that the RFID device is attached, and the device can also be visually inspected for possible damage. In addition, with the device enclosed within the pill, the pill itself may interfere with transmission/reception of signals, possibly requiring higher signal transmission power.

With present technologies, the circuitry for an RFID device is readily accommodated within an area 2.5 mm×2.5 mm square, including integrated antenna. Routine experimentation may be performed to determine if a device of that size has sufficient transmission power for the purposes of the invention. If not, larger and more powerful RFID devices are simply used. For any pill that may be too small to have a RFID device attached to its side surface, the pill may instead be attached to the side surface of the RFID device, with the pill/RFID assembly then enclosed in a sufficient quantity of gel material to ensure that the entire assembly is easily indigestible.

As noted above, the RFID devices are preferably coated with a material to render the device biocompatible and non-digestible. In this manner, the RFID device is eventually eliminated from the body as waste after the medication of the pill has been digested. In one example, the RFID device is potted in a ceramic or similar substance to ensure no biocompatibility problems. Parylene may also be suitable, as well as selected plastics. Techniques for encapsulating an RFID device for insertion into biological samples or corrosive environments are discussed in U.S. Pat. No. 5,963,132 to Yoakum, entitled "Encapsulated Implantable Transponder."

Figure 10:
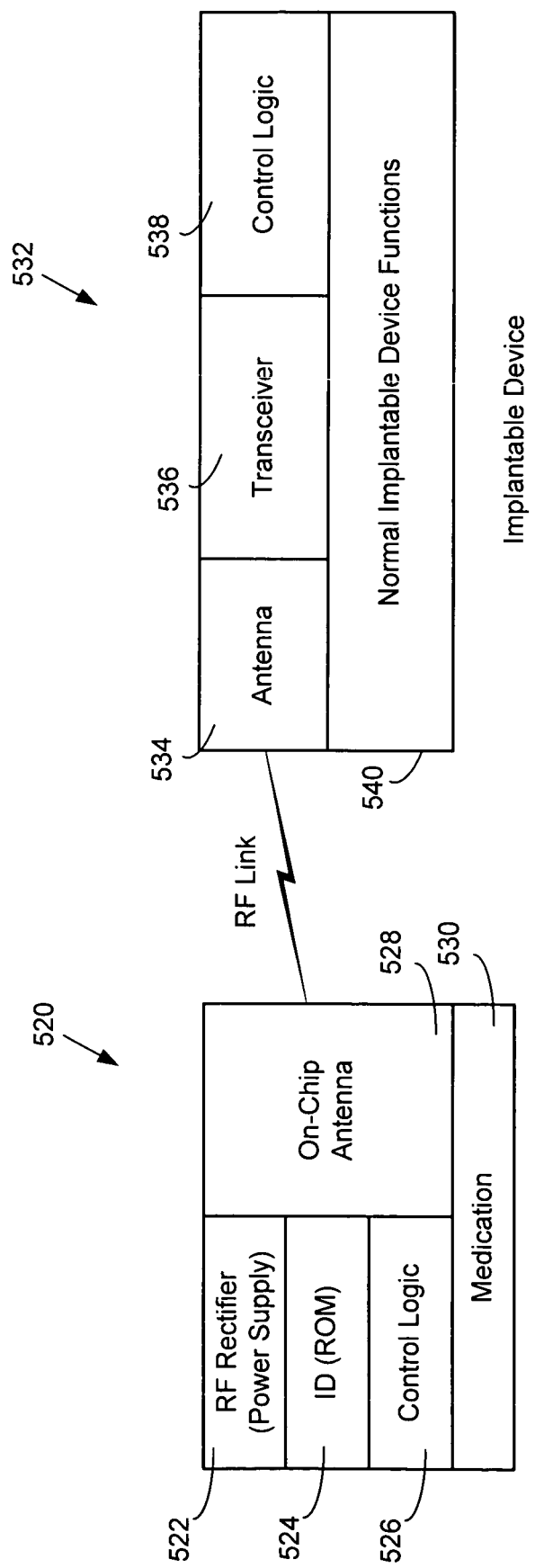
FIG. 10 is a diagram particularly illustrating functional components of a pill equipped with a passive RFID device for use with the system of FIG. 1.
Figure 11:
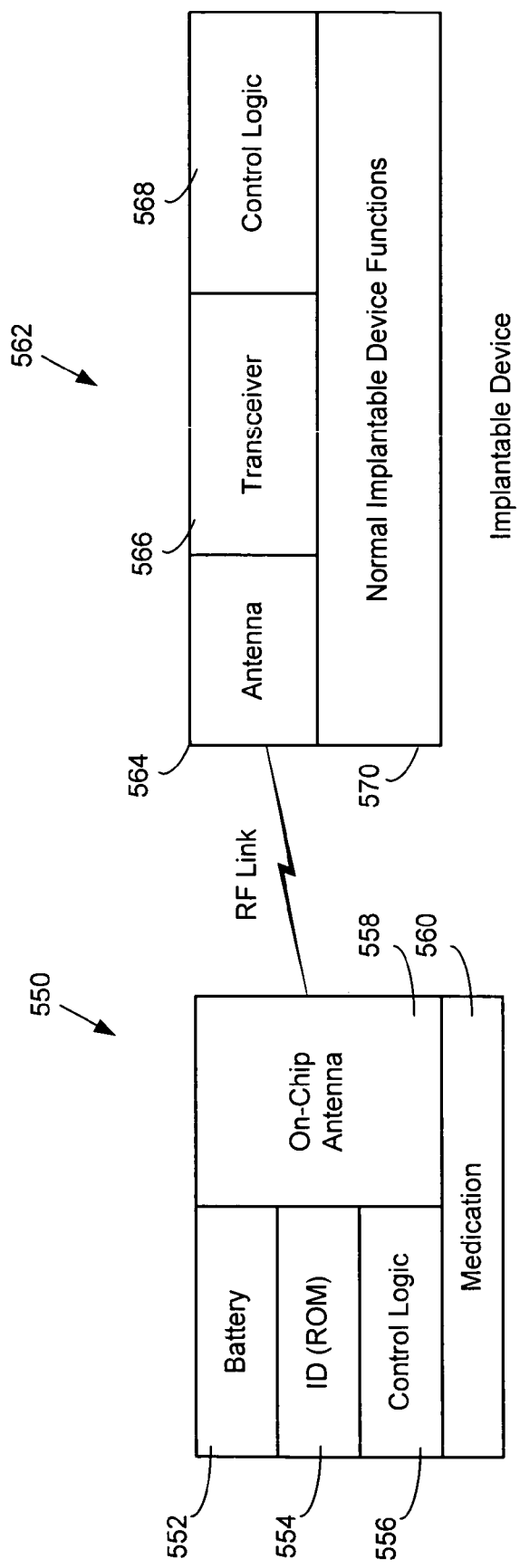
FIG. 11 is a block diagram particularly illustrating functional components of a pill equipped with an active RFID device for use with the system of FIG. 1.

Functional components for passive and active RFID devices (and the implantable device that receives signals therefrom) are illustrated within FIGS. 10 and 11. Briefly, passive RFID device 520 of FIG. 10 includes an RF rectifier 522 (which is used as a power supply), an ID circuit 524 (which stores the ID of the RFID tag), control logic 526 an-d an on-chip antenna 528. The ID circuit 524 may be a read-only memory (ROM) circuit. The medication to which the RFID device is attached is illustrated by way of block 530. The implanted device includes an antenna 534, a transceiver 536 and control logic 538 for controlling transmission and reception of signals from the RFID device. These components are in addition to normal functions of the device, such as pacing functions and the like, which are collectively represented by block 540. Briefly, in the passive RFID implementation, the control logic (538) of the implanted device controls the transceiver to deliver alternating current (AC) power to antenna 534 for transmission via an RF link to the antenna of the RFID device. AC power received by the on-chip antenna is rectified by the RF rectifier, which is then routed to the control logic of the RFID device, which uses the power to access the ID ROM to readout the RFID tag and to transmit the RFID tag via the on-chip antenna to the implanted device over the RF link. As noted above, low frequencies are preferably used. The RFID ID tag signal transmitted by the RFID device is received by the antenna of the implanted device and decoded by its transceiver. The control logic of the implanted device uses the RFID tag in accordance with the techniques described above to identify the particular medication being ingested, generate any necessary warning/reminder signals, adjust device functionality, etc.

Functional components for an active RFID device (and the implantable device that receives signals therefrom) is illustrated within FIG. 11. Many of the components are the same or similar to those of FIG. 10 will not be re-described. Briefly, active RFID device 550 of FIG. 11 includes an on-board battery 552, an ID circuit 554, control logic 556 and on-chip antenna 558. Whereas the antenna of the passive RFID device of FIG. 10 must be capable of receiving power from the pacer/ICD as well as transmitting RFID tag signals, with the active device of FIG. 11, power is instead provided by the on-board battery and hence antenna 558 is used only to transmit data. Accordingly, antenna 558 of FIG. 10 may differ in size and configuration from antenna 528 of FIG. 11. The medication to which the RFID device is attached is illustrated by way of block 560. The implanted device 562 includes an antenna 564, a transceiver 566 and control logic 568 for controlling reception of signals from the RFID device. These components are in addition to components performing the normal functions of the device, such as pacing functions and the like, which are collectively represented by block 570. Whereas antenna 534 of FIG. 10 for use with passive RFID devices must be capable of transmitting power to the RFID device, antenna 564 of FIG. 11 need only receive signals from the RFID device. Accordingly, if desired, antenna 564 of FIG. 11 may be configured with a different size and shape from antenna 534 of FIG. 10 so as to be optimized for receiving RFID signals only. Also, the transceiver and control logic of the active configuration of FIG. 11 may differ from corresponding components of the passive configuration of FIG. 10. Preferably, however, the antenna, transceiver and control logic of the implanted device are configured so as to operate with both passive and active RFID devices.

Exemplar Pacer/ICD

The aforementioned techniques may be exploited in connection with a wide variety of implantable devices. For the sake of completeness, a detailed description of a suitable pacer/ICD will now be provided with reference to FIGS. 12 and 13.

Referring first to FIG. 12, the figure provides a simplified block diagram of the pacer/ICD, which is a multi-chamber stimulation device capable of treating both fast and slow arrhythmias with stimulation therapy, including cardioversion, defibrillation, and pacing stimulation (as well as capable of detecting RFID tags, tracking medication intake based on the tags, controlling the generation of reminder/warning signals and adjusting therapy in response thereto.) To provide atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 624 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. With this configuration, biventricular pacing can be performed. Although only three leads are shown in FIG. 12, it should also be understood that additional stimulation leads (with one or more pacing, sensing and/or shocking electrodes) may be used in order to efficiently and effectively provide pacing stimulation to the left side of the heart or atrial cardioversion and/or defibrillation. The leads are also employed for sensing ID tag signals from medications equipped with active ID transmitters.

Figure 13:
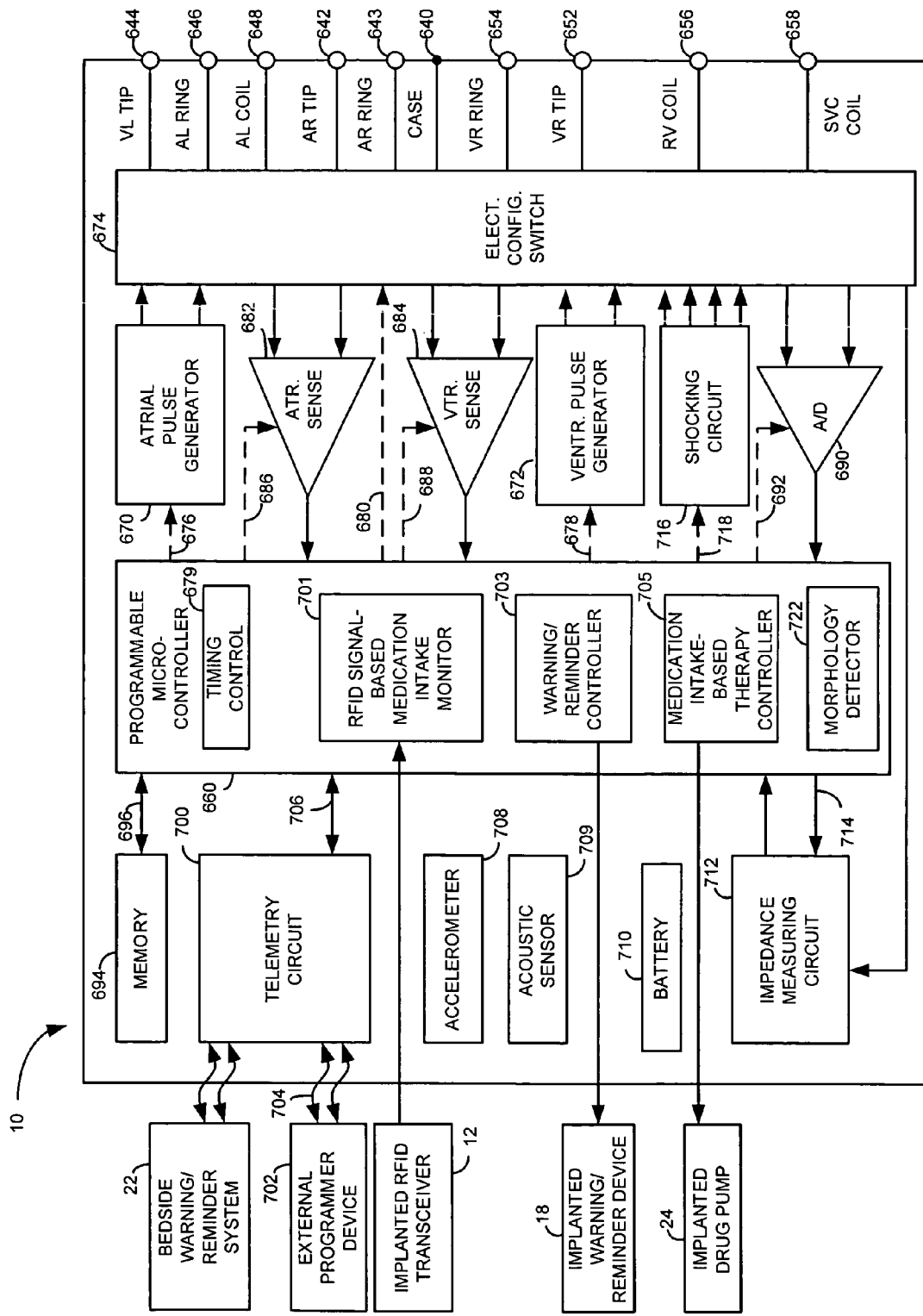
FIG. 13 is a block diagram illustrating internal functional components of the device of FIG. 12, which includes components for automatically monitor drug intake via RFID signals.

A simplified block diagram of internal components of pacer/ICD 10 is shown in FIG. 13. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 640 for pacer/ICD 10, shown schematically in FIG. 13, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 643. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial tip electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 632, right ventricular ring electrode 634, the RV coil electrode 636, and the SVC coil electrode 638, respectively. Separate terminals (not shown) may be provided for connecting the external RFID device 12, the implanted warning/reminder device 18 and the implanted drug pump 24, which are instead shown coupled directly to internal functional components of the pacer/ICD that control these devices.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 13, an atrial pulse generator 670 and a ventricular/impedance pulse generator 672 generate pacing stimulation pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart and for sensing RFID tag signals received from active RFID devices. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the coronary sinus lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor 708, commonly referred to as a "rate-responsive" sensor because it is typically used to adjust pacing stimulation rate according to the exercise state of the patient. However, the physiological sensor 708 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV Delay, V-V Delay, etc.) at which the atrial and ventricular pulse generators, 670 and 672, generate stimulation pulses. While shown as being included within pacer/ICD 10, it is to be understood that the accelerometer 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc. An accelerometer is preferred as it allows patient movement and patient posture to be detected for use in verifying patient swallowing to aid in detection of RFID signals. An acoustic sensor 709 is preferably also employed for this purpose.

The pacer/ICD additionally includes a battery 710, which provides operating power to all of the circuits shown in FIG. 13. The battery 710 may vary depending on the capabilities of pacer/ICD 10. If the system only provides low voltage therapy, a lithium iodine or lithium copper fluoride cell may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, pacer/ICD 10 is preferably capable of high voltage therapy and batteries or other power sources appropriate for that purpose are employed.

As further shown in FIG. 13, pacer/ICD 10 is shown as having an impedance measuring circuit 712 which is enabled by the microcontroller 660 via a control signal 714. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when-the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Microcontroller 60 also includes an RFID signal-based medication intake monitor 701 for automatically monitoring the intake of drugs prescribed to the patient using the techniques described above. In this regard, the medication intake monitor 701 is operative to control RFID tag detection based on signals received from the RFID transceiver via either active or passive RFID techniques, already described. For passive RFID, the medication intake monitor processes data received from accelerometer 708 and the acoustic sensor 709 to detect when the patient is in the act of swallowing and, if so, activates RFID transceiver 12 to transmit power to any RFID device being swallowed at that time. Responsive RFID signals, if any, sensed by RFID transceiver 12 are processed by medication intake monitor 701 to decode the RFID tag. For active RFID, the RFID transceiver monitors for RFID signals from any active RFID being ingested and forwards the signals to medication intake monitor to decode the ID tag. The controller uses the techniques described above to verify that the RFID tag identities a drug that had been prescribed to the patient and also periodically identifies any drugs that had been prescribed but had not been ingested in a timely manner. A warning/reminder controller 703 operates to generate appropriate reminder or warning signals, using the techniques described above, for forwarding to the implanted reminder/warning device 18 or to the bedside warning/reminder system 22. A medication-base therapy controller 705 operates to control therapy in response to drug intake (or lack thereof) via implanted drug pump 24 or via pacing using the leads of the pacer/ICD. In an alternative embodiment, analysis of the RFID signals is performed by the external programmer 702 or the bedside monitoring system 22 and so medication intake monitor 701 merely forwards RFID tag data via telemetry circuit 700 to the appropriate external device.

What have been described thus far are primarily techniques for use with medications tagged with RFID devices. Other types of EID devices (i.e. non-RF EID devices) may instead be used. In the following, an alternative implementation is discussed that exploits signals sent via biphasic current pulses that are conducted through patient tissue. In other words, instead of using RF signals (which propagate as electromagnetic waves) to transmit data from the pill to the implanted system, the alternative implementation instead uses pulses of electrical current that are conducted through the tissues of the body. Many of the features of the alternative implementation are the same as with the RFID-based implantation already described and so the alternative implementation will only be summarized.

Biphasic Current Pulse-based Medication Intake Monitoring System

Figure 14:
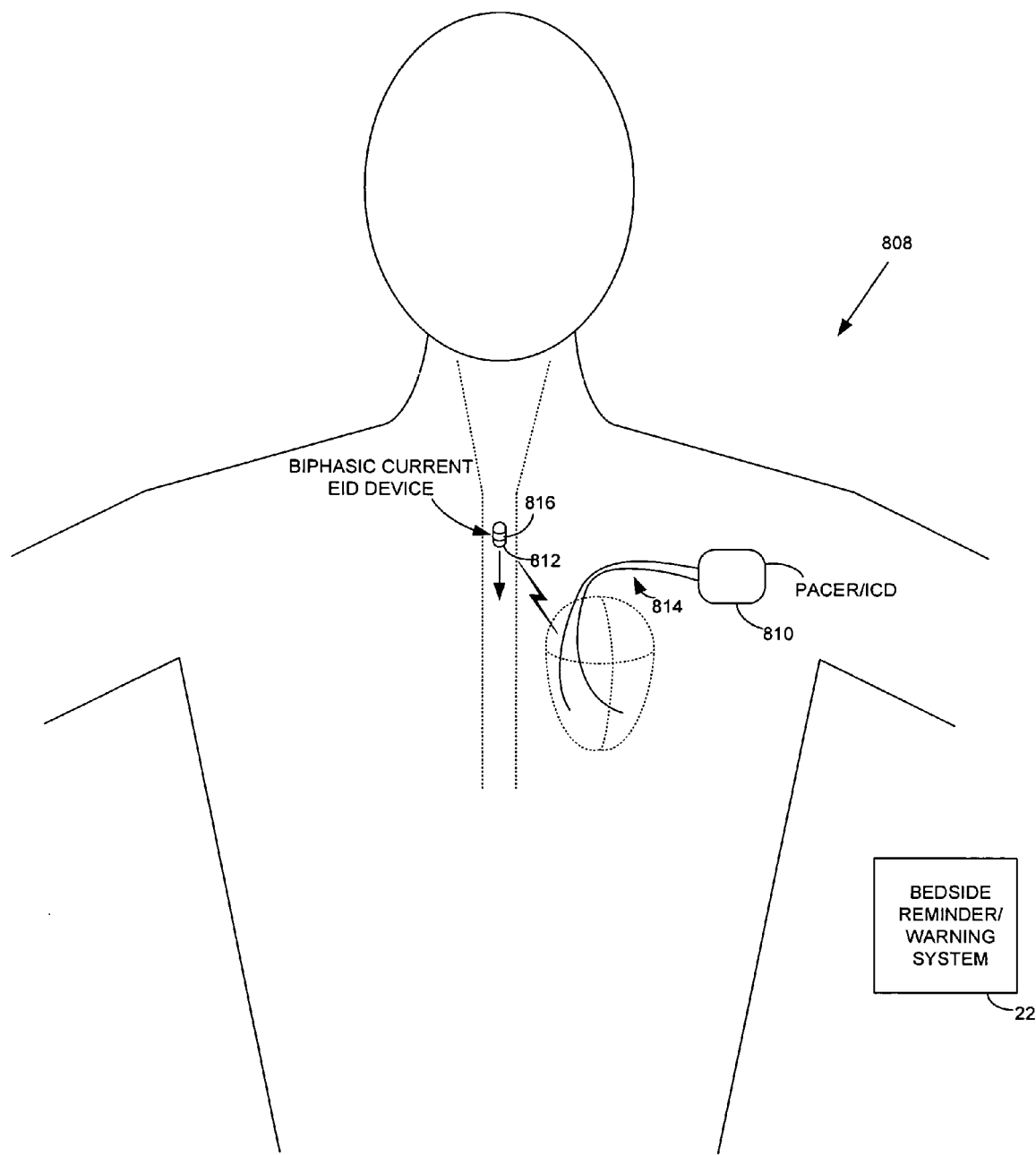
FIG. 14 illustrates pertinent components of an implantable medication monitoring system having a pacemaker or ICD capable of detecting ID tag signals transmitted through patient tissue as biphasic current pulses.

FIG. 14 illustrates an implantable medical system 808 having a pacer/ICD 810 capable of detecting the ingestion of medication 812 via an ID tag signal transmitted in the form of biphasic current pulses conducted through the tissues of the body to a set of leads 814 of the implanted device. (Only two leads are shown in FIG. 14. A full set of leads is illustrated in FIG. 12.) The medication being ingested includes an EID device 816, which includes circuitry for storing the ID tag and for generating the biphasic current pulses. The pacer/ICD uses the ID tag to verify the correct drug/dosage of ingested medications and then generates and forwards appropriate warning signals to a bedside monitor/warning system 22, in accordance with techniques already described. Pacing therapy may also be adjusted based on whether the correct drug/dosage of the medications has been ingested. Although not shown in FIG. 14, an implantable warning device may also be provided, as shown in FIG. 1, for delivering warning signals internally. In addition, an implantable drug pump, also shown in FIG. 1, may be provided for delivering medications directly to the patient. Unlike the embodiment of FIG. 1, no RFID transceiver is used.

The system of FIG. 14 is a passive system, in that the EID device of the pill being ingested generates the biphasic current pulses using power from an on-board battery. The ID tag is encoded for transmission as a sequence of pulses, using otherwise conventional data encoding and transmission techniques. The leads of the device are used to detect the current pulses so that the ID can be decoded. That is, a pair of electrodes within the leads, such as the right and left ventricular tip electrodes, is selected for use as a detection "antenna" for detecting the current pulses. Alternatively, the device may be used as one of the electrodes. In any case, otherwise conventional techniques for use in detecting thoracic impedance using pacing leads may be used for detecting the current pulses as well. Impedance detection techniques are set forth in, for example, U.S. Pat. No. 6,658,294 to Zadeh, et al., entitled "Implantable Cardiac Device Having an Impedance Monitoring Circuit and Method." Preferably, normal pacing and sensing functions of the leads are temporarily suspended while the leads are used to detect current pulses, i.e. the normal atrial and ventricular sense amplifiers are blanked during the ID receive time to prevent possible false P and R sensing and subsequent inadvertent pacing inhibition. The techniques described above for use in detecting when the patient is swallowing are preferably employed and the leads are only enabled for ID detection during periods of time when it appears the patient may be in the act of swallowing medication.

Figure 15:
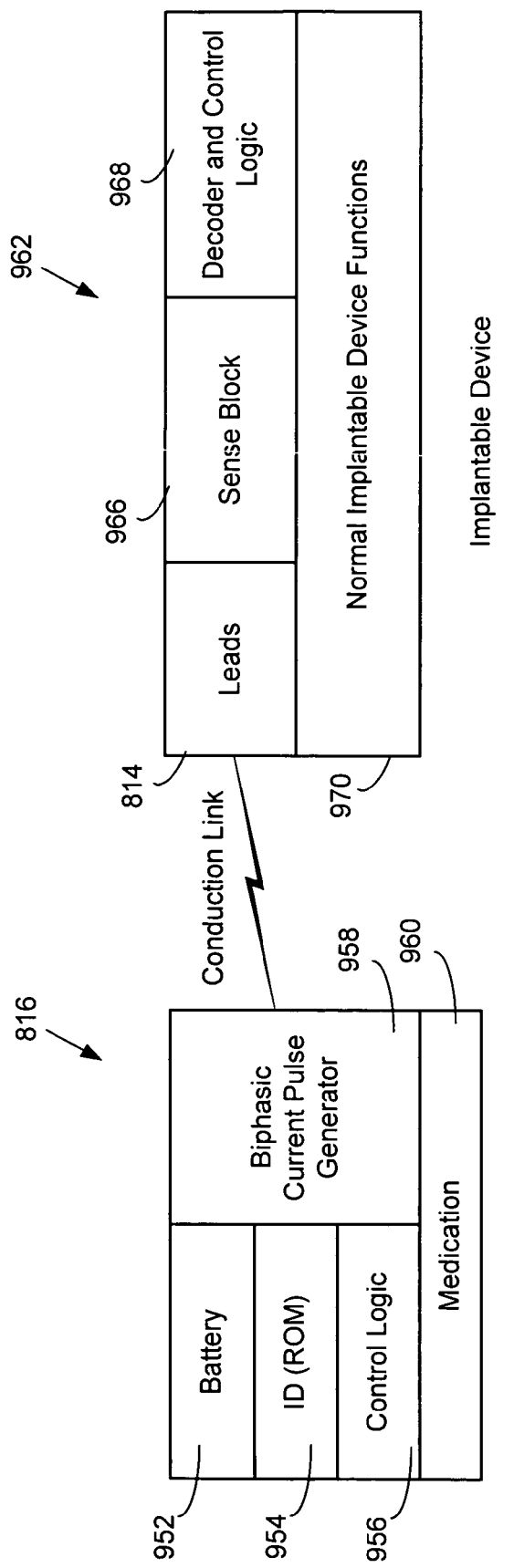
FIG. 15 is a block diagram particularly illustrating functional components of a pill equipped with biphasic current pulse generator for use with the system of FIG. 14.

Functional components for EID device 816 (and the implantable device that receives signals therefrom) are illustrated within FIG. 15. Many of the components are the same or similar to those of the active RFID implementation of FIG. 11 and will not be re-described. Briefly, biphasic current EID device 816 includes an on-board battery 952, an ID circuit 954 and control logic 956. Rather than employing an on-chip antenna, EID device 950 instead uses a biphasic current pulse generator 958, which includes a pair of electrodes spaced as widely apart on the medication as possible. The medication to which the EID device is attached is illustrated by way of block 960. The implanted device, rather than employing an RFID transceiver as in the RFID embodiments described above, instead uses one or more cardiac pacing leads 814 to sense the current pulse signals. A sense block 966 is provided for sensing current pulse signals picked up by the leads, including ID signals. Sense block 966 is separate from the sense amplifiers that are used for sensing electrical cardiac signals (i.e. sense amplifiers 682 and 684 discussed above). In other words, the implanted device includes a separate set of sense amplifiers specifically configured for sensing the current pulses. A decoder and control logic unit 968 decodes the current pulse ID signals to identify the ID tag. The decoder and control logic unit then uses the ID tag in accordance with the techniques described above to identify the particular medication being ingested, generate any necessary warning/reminder signals, adjust device functionality, etc. Normal functions of the device, such as normal sensing and pacing functions, are collectively represented by block 970.

The various functional components of the exemplary system may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. A method for use in monitoring the ingestion of pills by a patient in which an implantable medical system is implanted, the method comprising:
    sensing a signal transmitted by an individual pill being ingested;
    detecting ingestion of the pill based on the sensed signal;
    wherein the individual pill is equipped with radio frequency identification (RFID) device and wherein sensing the signal transmitted by the pill comprises sensing an RFID signal transmitted by the RFID device of the pill;
    wherein the individual pill is equipped with a passive RFID device and wherein sensing signals comprises:
    transmitting a power signal to the passive RFID device of the pill;
    receiving a responsive signal returned by the passive RFID device of the pill; and
    wherein the implantable system is equipped to detect and classify patient movement and wherein transmitting a power signal to the passive RFID device is triggered by detection of patient motion that is consistent with the swallowing of a pill.

2. A method for use in monitoring the ingestion of pills by a patient in which an implantable medical system is implanted, the method comprising:
    sensing a signal transmitted by an individual pill being ingested;
    detecting ingestion of the pill based on the sensed signal;
    wherein the individual pill is equipped with radio frequency identification (RFID) device and wherein sensing the signal transmitted by the pill comprises sensing an RFID signal transmitted by the RFID device of the pill;
    wherein the individual pill is equipped with a passive RFID device and wherein sensing signals comprises:
    transmitting a power signal to the passive RFID device of the pill;
    receiving a responsive signal returned by the passive RFID device of the pill; and
    wherein the implantable system is equipped to detect internal patient sounds and wherein transmitting a power signal to the passive RFID device is triggered by detection of sounds consistent with swallowing a pill.

3. A method for use in monitoring the ingestion of pills by a patient in which an implantable medical system is implanted, the method comprising:
    sensing a signal transmitted by an individual pill being ingested;
    detecting ingestion of the pill based on the sensed signal;
    wherein the individual pill is equipped with radio frequency identification (RFID) device and wherein sensing the signal transmitted by the pill comprises sensing an RFID signal transmitted by the RFID device of the pill;
    wherein the individual pill is equipped with a passive RFID device and wherein sensing signals comprises:
    transmitting a power signal to the passive RFID device of the pill;
    receiving a responsive signal returned by the passive RFID device of the pill; and
    wherein the implantable system is equipped to detect and classify patient posture and wherein transmitting a power signal to the passive RFID device is not performed unless patient posture is consistent with the swallowing of a pill.

4. A method for use in monitoring the ingestion of pills by a patient in which an implantable medical system is implanted, the method comprising:
    sensing a signal transmitted by an individual pill being ingested;
    detecting ingestion of the pill based on the sensed signal;
    wherein the individual pill is equipped with radio frequency identification (RFID) device and wherein sensing the signal transmitted by the pill comprises sensing an RFID signal transmitted by the RFID device of the pill;
    wherein the individual pill is equipped with a passive RFID device and wherein sensing signals comprises:
    transmitting a power signal to the passive RFID device of the pill;
    receiving a responsive signal returned by the passive RFID device of the pill; and
    wherein the implantable system is equipped to detect patient sleep and wherein transmitting a power signal to the passive RFID device is not performed if the patient is asleep.

5. A method for use in monitoring the ingestion of pills by a patient in which an implantable medical system is implanted, the method comprising:
    sensing a signal transmitted by an individual pill being ingested;
    detecting ingestion of the pill based on the sensed signal;
    wherein the individual pill is equipped with radio frequency identification (RFID) device and wherein sensing the signal transmitted by the pill comprises sensing an RFID signal transmitted by the RFID device of the pill;
    wherein the RFID signal includes an RFID tag sufficient to identify the medication being ingested and wherein detecting ingestion of a pill comprises:
    decoding the RFID tag of the RFID signal;
    comparing the decoded RFID tag against a database listing individual RFID tags and the particular medications associated therewith; and generating a signal indicative of the particular medication being ingested if the decoded RFID tag matches an RFID tag stored in the database; and further comprising:

determining whether the medication being ingested is among medications prescribed to the patient; and generating a warning signal if the medication being ingested is not among medications prescribed to the patient.

6. The method of claim 5 wherein whether the medication being ingested is among medications prescribed to the patient comprises comparing the medication being ingested against a database listing medications prescribed to the patient.

7. The method of claim 5 wherein the implanted system includes an implanted warning device for generating a perceptible signal and wherein generating a warning signal is performed by activating the implanted warning device.

8. The method of claim 5 wherein the implanted system is used in conjunction with an external warning device and wherein generating a warning signal is performed by transmitting a warning signal to the external warning device.

9. A method for use in monitoring the ingestion of pills by a patient in which an implantable medical system is implanted, the method comprising:

sensing a signal transmitted by an individual pill being ingested;

detecting ingestion of the pill based on the sensed signal;

wherein the individual pill is equipped with radio frequency identification (RFID) device and wherein sensing the signal transmitted by the pill comprises sensing an RFID signal transmitted by the RFID device of the pill;

wherein the RFID signal includes an RFID tag sufficient to identify the medication being ingested and wherein detecting ingestion of a pill comprises:

decoding the RFID tag of the RFID signal;

comparing the decoded RFID tag against a database listing individual RFID tags and the particular medications associated therewith;

generating a signal indicative of the particular medication being ingested if the decoded RFID tag matches an RFID tag stored in the database;

wherein the RFID tag is also sufficient to identify the dosage of the medication being ingested and wherein detecting ingestion of a pill also comprises generating a signal indicative of the dosage being ingested; and further comprising:

determining whether the dosage being ingested is a dosage prescribed to the patient; and generating a warning signal if the dosage being ingested is not the dosage prescribed to the patient.

10. The method of claim 9 wherein determining whether the dosage being ingested is the dosage prescribed to the patient comprises comparing the dosage being ingested against a database listing the dosage prescribed to the patient for the particular medication being ingested.

11. A method for use in monitoring the ingestion of pills by a patient in which an implantable medical system is implanted, the method comprising:

sensing a signal transmitted by an individual pill being ingested;

detecting ingestion of the pill based on the sensed signal;

wherein the individual pill is equipped with radio frequency identification (RFID) device and wherein sensing the signal transmitted by the pill comprises sensing an RFID signal transmitted by the RFID device of the pill;

wherein the RFID signal includes an RFID tag sufficient to identify the medication being ingested and wherein detecting ingestion of a pill comprises:

decoding the RFID tag of the RFID signal;

comparing the decoded RFID tag against a database listing individual RFID tags and the particular medications associated therewith;

generating a signal indicative of the particular medication being ingested if the decoded RFID tag matches an RFID tag stored in the database;

wherein the RFID tag is also sufficient to identify the dosage of the medication being ingested and wherein detecting ingestion of a pill also comprises generating a signal indicative of the dosage being ingested; and further comprising recording information identifying the dosage of the medication being ingested.

12. A method for use in monitoring the ingestion of pills by a patient in which an implantable medical system is implanted, the method comprising:

sensing a signal transmitted by an individual pill being ingested:

detecting ingestion of the pill based on the sensed signal;

determining whether the patient has failed to take prescribed medications;

wherein determining whether the patient has failed to take prescribed medications comprises:

accessing a database listing medications prescribed to the patient and a time frame in which the medication is expected to be taken; and generating a warning signal if there is no detection of ingestion of the prescribed medication within the expected time frame.

13. A method for use in monitoring the ingestion of pills by a patient in which an implantable medical system is implanted, the method comprising:

sensing a signal transmitted by an individual pill being ingested;

detecting ingestion of the pill based on the sensed signal;

determining whether the patient has failed to take prescribed medications;

controlling therapy in response to failure to take a prescribed medication;

wherein the prescribed medication includes heart medication, wherein the implantable system is equipped to perform pacing therapy and wherein controlling therapy in response to failure to take the prescribed medication comprises controlling pacing therapy in an attempt to compensate for failure to take the prescribed medication.

14. A method for use in monitoring the ingestion of pills by a patient in which an implantable medical system is implanted, the method comprising:

sensing a signal transmitted by an individual pill being ingested;

detecting ingestion of the pill based on the sensed signal;

determining whether the patient has failed to take prescribed medications;

controlling therapy in response to failure to take a prescribed medication;

wherein the prescribed medication includes medication provided to prevent atrial fibrillation (AF), wherein the implantable system is equipped to deliver atrial overdrive pacing to prevent AF and wherein controlling therapy in response to failure to take the prescribed medication comprises activating overdrive pacing.

15. A method for use in monitoring the ingestion of pills by a patient in which an implantable medical system is implanted, the method comprising:
- sensing a signal transmitted by an individual pill being ingested;
- detecting ingestion of the pill based on the sensed signal;
- determining whether the patient has failed to take prescribed medications;
- controlling therapy in response to failure to take a prescribed medication;
- wherein the implantable system is equipped with a drug pump provided with a quantity of medication and wherein controlling therapy in response to failure to take prescribed medication comprises controlling the drug pump to deliver a quantity of medication stored therein.

* * * * *